United States Patent [19]

Allen et al.

[11] Patent Number: 5,656,750
[45] Date of Patent: Aug. 12, 1997

[54] PROCESSES FOR THE PREPARATION OF SQUARYLIUM DYES

[75] Inventors: Richard M. Allen, Norton; Peter K. Chu, Acton, both of Mass.

[73] Assignee: Polaroid Corporation, Cambridge, Mass.

[21] Appl. No.: 485,240

[22] Filed: Jun. 6, 1995

Related U.S. Application Data

[62] Division of Ser. No. 235,483, Apr. 29, 1994, Pat. No. 5,492,795, which is a division of Ser. No. 979,250, Nov. 20, 1992, Pat. No. 5,354,873, which is a continuation-in-part of Ser. No. 795,034, Nov. 20, 1991, Pat. No. 5,227,498.

[51] Int. Cl.⁶ .............. C07D 311/58; C07D 309/34; C07D 335/06; C07D 345/00
[52] U.S. Cl. .............. 540/1; 544/145; 544/149; 544/151; 546/66; 546/196; 546/207; 548/454; 548/517; 548/525; 549/5; 549/13; 549/23; 549/28; 549/404; 549/408; 549/415; 549/416; 549/417; 549/419; 549/218; 549/220; 549/398
[58] Field of Search .............. 549/5, 13, 23, 549/28, 404, 408, 415, 416, 417, 419, 218, 220, 398; 548/454, 517, 525; 546/66, 196, 207; 544/145, 149, 151; 540/1

[56] References Cited

U.S. PATENT DOCUMENTS

| | | | |
|---|---|---|---|
| 4,343,948 | 8/1982 | Kawamura et al. | 549/13 |
| 4,508,811 | 4/1985 | Gravesteijn et al. | 430/270 |
| 4,602,263 | 7/1986 | Borrer et al. | 346/201 |
| 4,663,518 | 5/1987 | Borrer et al. | 235/487 |
| 4,720,449 | 1/1988 | Borrer et al. | 430/338 |
| 4,826,976 | 5/1989 | Borrer et al. | 544/58.4 |
| 4,960,901 | 10/1990 | Borrer et al. | 548/207 |
| 5,153,169 | 10/1992 | Freedman et al. | 503/209 |

FOREIGN PATENT DOCUMENTS

| | | |
|---|---|---|
| 58-220143 | 12/1983 | Japan . |
| 61-167681 | 7/1986 | Japan . |

OTHER PUBLICATIONS

Chemical Abstracts 74:3479b (1971).
Chemical Abstracts 91:140384g and 140385h (1979).
Cohen S. and Cohen, S. G., J. Am. Chem. Soc., 88, 1533 (1966).
Gerecht et al., Chem. Ber. 117(8), 2714–29 (1984).
Himbert et al., Chem. Ber. 117(2), 642–53 (1984).
Kuramoto et al., Dyes and Pigments, 11, 21–35 (1989).
Maahs, et al., "Syntheses and Derivatives of Squaric Acid", Angew. Chem. Int. Ed., 5, 888–893 (1966).
Schmidt, A. H. and Reid, W., Synthesis, 1978, 869.
Schmidt, A.H., The Chemistry of Squaraines, in West, R. (ed.), Oxocarbons, Academic Press (1980).
Seitz et al., Arch. Pharm. (Weinheim) 310, 549–59 (1977).
Smitney, J.A.C.S. 82, 1793 (1960).
West, R., Israel J. Chem., 20, 300–307 (1980).

*Primary Examiner*—Richard L. Raymond
*Attorney, Agent, or Firm*—David J. Cole

[57] ABSTRACT

Squarylium compounds of the formula:

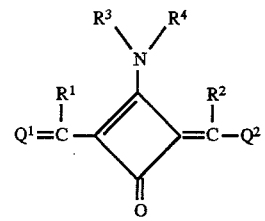

(in which $Q^1$ and $Q^2$ are each a chromophoric group having an aromatic unsaturated system conjugated with the squarylium ring and such that in the compounds of formulae $Q^1CH_2R^1$ and $Q^2CH_2R^2$ the methylene hydrogens are active hydrogens, $R^1$ and $R^2$ are each independently a hydrogen atom or an aliphatic or cycloaliphatic group, and $R^3$ and $R^4$ are each independently a hydrogen atom, or an acyl, aliphatic, cycloaliphatic, aromatic or heterocyclic group, subject to the proviso that one of $R^3$ and $R^4$ may be an amino or substituted amino group, or one of $R^3$ and $R^4$ is a hydrogen atom and the other is an organosulfonyl group, or $R^3$ and $R^4$ together with the intervening nitrogen atom form a nitrogenous heterocyclic ring) are useful as near infra-red absorbers. The presence of the amino group on the squarylium ring enables minor changes in absorption wavelength to be achieved by modifications of this group, and also allows functional groups to be incorporated into the dye without changing the chromophoric groups.

2 Claims, 6 Drawing Sheets

PROCESSES FOR THE PREPARATION OF SQUARYLIUM DYES

REFERENCE TO PARENT APPLICATION

This application is a division of application Ser. No. 08/235,483, filed Apr. 29, 1994 (now U.S. Pat. No. 5,492,795), which is a division of application Ser. No. 07/979,250, filed Nov. 20, 1992 (now U.S. Pat. No. 5,354,873), which in turn in a continuation-in-part of application Ser. No. 07/795,034, filed Nov. 20, 1991 (now U.S. Pat. No. 5,227,498).

BACKGROUND OF THE INVENTION

1. Field of the Invention

This invention relates to squarylium dyes, and processes and intermediates for the preparation thereof. More specifically, it relates to such dyes and intermediates in which the squarylium ring bears an amino or substituted amino group, and also certain other intermediates useful for the preparation of the aforementioned dyes.

2. References to Related Applications

U.S. Pat. No. 5,405,976 and International Application No. PCT/US91/08695 (Publication No. WO 92/09661) describe dyes comprising an inner salt of a compound of the formula:

wherein:

$Q^1$ is a 4-(benz[b]-4H-pyrylium)methylidene, 4-(benz[b]-4H-thiopyrylium)methylidene or 4-(benz[b]-4H-selenopyrylium)methylidene grouping;

Z is a 1,3-(2-hydroxy-4-oxo-2-cyclobutylidene) or 1,3-(2-hydroxy-4,5-dioxo-2-cyclopentylidene) ring; and $Q^2$ is a 4-(benz[b]-4H-pyran-4-ylidene)methyl, 4-(benz[b]-4H-thiopyran-4-ylidene)methyl or 4-(benz[b]-4H-selenopyran-4-ylidene)methyl grouping;

wherein at least one of the groupings $Q^1$ and $Q^2$ carries at its 2-position a substituent in which a non-aromatic carbon atom is bonded directly to the benzpyrylium, benzthiopyrylium or benzselenopyrylium nucleus, subject to the proviso that if this 2-substituent contains an aromatic nucleus, this aromatic nucleus is not conjugated with the benzpyrylium, benzthiopyrylium or benzselenopyrylium nucleus to which it is attached. These dyes have high absorptions in the near infra-red, and improved solubility in semi-polar solvents and plastics. The dyes disclosed in these applications include certain infra-red dyes which can be used in the thermal imaging medium described below with reference to FIG. 6.

Copending application U.S. Ser. No. 07/696,222, filed May 6, 1991 (now U.S. Pat. No. 5,231,190) and assigned to the same assignee as the present application, and the corresponding European Application No. 92107574.3, describe and claim the squarylium compounds of formulae D, E, J and K described below with reference to FIG. 1, together with similar compounds containing different heterocyclic nuclei, and squarylium compounds of the formula:

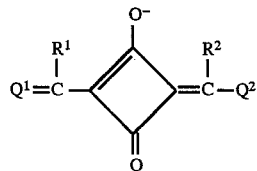

wherein $Q^1$ and $Q^2$ are each independently a heterocyclic nucleus such that in the compounds of formulae $Q^1CH_2R^1$ and $Q^2CH_2R^2$ the methylene hydrogens are active hydrogens, the atoms of $Q^1$ and $Q^2$ which are bonded directly to the $CR^1$ and $CR^2$ groupings respectively each being part of an aromatic ring, and $Q^1$ and $Q^2$ are different, and $R^1$ and $R^2$ are each independently a hydrogen atom or an aliphatic or cycloaliphatic group. The disclosure of this copending U.S. application is discussed below in more detail with reference to FIG. 1.

Copending applications U.S. Ser. Nos. 07/695,641 (now U.S. Pat. No. 5,342,816) 07/696,196 (see also the corresponding European Application No. 92107576.8 (Publication No. 512,476)) and 07/695,932 (now U.S. Pat. No. 5,153,169, issued Oct. 6, 1992), all filed May 6, 1991 and all assigned to the same assignee as the present application, describe and claim imaging media comprising a color-forming layer comprising a thermal color-forming composition adapted to undergo a change of color upon increase in the temperature of the color-forming layer above a color-forming temperature for a color-forming time. Preferred imaging media described in these three applications comprise three separate color-forming layers containing yellow, cyan and magenta thermal color-forming compositions; each of these color-forming compositions comprises a color-forming compound which undergoes a change of color upon heating above the color-forming temperature for the color-forming time, and an infra-red absorber capable of absorbing infra-red radiation and thereby generating heat in the color-forming layer. The three color-forming layers use infra-red absorbers absorbing at differing wavelengths so that each color-forming layer can be imaged independently; for example, specific imaging media disclosed in these three applications use infra-red absorbers having peak absorptions at approximately 792, 822 and 869 nm.

Copending application U.S. Ser. No. 07/795,341, filed Nov. 20, 1991 (now U.S. Pat. No. 5,206,206), and assigned to the same assignee as the present application, describes infra-red dyes generally similar to those of the present invention, but in which the 2-substituent on the squarylium ring has a carbon atom directly bonded to the squarylium ring.

Copending application U.S. Ser. No. 07/795,101, filed Nov. 20, 1991 and assigned to the same assignee as the present application describes and claims thermal imaging media generally similar to those described in the aforementioned applications U.S. Ser. Nos. 07/695,641; 07/696,196 and 07/695,932 but in which at least one imaging layer contains a metal cation. Preferred imaging media described in this application have imaging layers containing zinc acetate, as described below with reference to FIG. 6.

The disclosures of all the aforementioned copending U.S. applications and patents are herein incorporated by reference.

3. Description of the Prior Art

It is known that compounds in which two chromophoric groups are linked by a pentamethine chain, the three central carbon atoms of which form part of a squarylium ring are useful as dyes, especially near infra-red dyes. (The term "near infra-red" is used herein to mean electromagnetic radiation having a wavelength of about 700 to about 1200 nm.)

The term "chromophoric group" is used herein to mean a group containing a plurality of conjugated unsaturated linkages arranged so that the unsaturated linkages are conjugated with the squarylium ring via the unsaturated ($sp^2$) meso carbon atom lying between the chromophoric group and the squarylium ring, the chromophoric group being such that the squarylium dye has substantial absorption of visible or infra-red radiation.

For example, Japanese Patent Application No. 103,604/82 (Publication No. 220,143/83, published Dec. 21, 1983), discloses a broad class of bis-heterocyclic pentamethine dyes in which the central three carbon atoms of the pentamethine chain form part of a squarylium or croconylium ring. The heterocyclic nuclei can be pyrylium, thiopyrylium, selenopyrylium, benzpyrylium, benzthiopyrylium, benzselenopyrylium, naphthopyrylium, naphthothiopyrylium or naphthoselenopyrylium nuclei, which can be substituted with alkyl, alkoxy, aryl or styryl groups.

Japanese Patent Application No. 60-8730 (Publication No. 167,681/86, published Jul. 29, 1986), discloses bis(4-benz[b]thiopyrylium) pentamethine dyes in which the central three carbon atoms of the pentamethine chain form part of a squarylium ring. The dyes are intended for use as infra-red absorbers.

U.S. Pat. No. 4,508,811, issued Apr. 2, 1985, describes an optical recording element in which the recording layer comprises a bis(2,6-dialkyl)-pyrylium or -thiopyrylium squarylium salt.

The squarylium dyes disclosed in these Japanese applications and U.S. patent are capable of achieving high extinction coefficients in the near infra-red range. However, such squarylium dyes suffer from a number of disadvantages. Many of these prior art dyes have low solubility in most plastics and/or in semi-polar solvents (for example, methyl ethyl ketone and methylene chloride) from which they need to be deposited to form imaging media. Thus, it is difficult to dissolve or disperse the absorber in a plastic without forming large aggregates and without adversely affecting other properties of the plastic.

A related disadvantage is that, unless specific functional groups are provided on the chromophoric groups (and the presence of such functional groups on the chromophoric groups may cause problems in the synthesis of the compounds from which the chromophoric groups are derived, or in the condensation of these compounds with squaric acid or its derivatives to form the final dyes), there is no convenient site (or "handle") on the squarylium dye for attachment of functional groups. Attachment of functional groups to the squarylium ring may be desirable, for example, to change the solubility of the dye in, or its compatibility with, various media, or to permit the dye to be chemically bonded to other materials.

Thirdly, among the squarylium dyes disclosed in these Japanese applications and U.S. patent, it may be difficult to find a dye which absorbs at the precise wavelength required for a particular application. For example, when choosing infra-red absorbers for use in imaging media such as those described in the aforementioned applications U.S. Ser. Nos. 07/695,641; 07/696,196 and 07/695,932, the need for independent addressing of the three color-forming layers, coupled with the widths of the peaks (typically the full-width-half-maximum (FWHM) of these peaks is about 35–40 nm) and the limited wavelength range over which present semiconductor lasers can be produced economically, mean that it is often necessary to find an infra-red absorber which has an absorption peak within a very narrow range (say 10–15 nm) and which meets all the other requirements of stability, solubility and compatibility with other components of the imaging medium required for use in such an imaging medium. It is often difficult if not impossible to find a squarylium dye from among those disclosed in the Japanese applications and U.S. patent which absorbs within such a narrow wavelength range.

The aforementioned disadvantages of earlier prior art squarylium dyes are greatly reduced in the dyes described in the aforementioned applications U.S. Ser. Nos. 07/616,639, 07/795,038 and 07/696,222. The 2-non-aromatic substituted dyes described in applications U.S. Ser. Nos. 07/616,639 and 07/795,038 are substantially more soluble than the corresponding 2-phenyl dyes, while the asymmetric dyes which can be synthesized in good yields by the processes described in application U.S. Ser. No. 07/696,222 greatly ease the task of finding a dye which absorbs at a desired wavelength, since the ability to change the two chromophoric groups independently gives an additional degree of freedom, as compared with earlier dyes in which the two chromophoric groups were the same. However, neither of these copending applications describes dyes in which functional groups are provided on the squarylium ring itself. Furthermore, there are still situations in which it would be advantageous to provide dyes with even greater solubility in certain media than those described in applications U.S. Ser. Nos. 07/616,639 and 07/795,038, and it would also be advantageous to provide some way in which the dyes disclosed in applications U.S. Ser. Nos. 07/616,639, 07/795,038 and 07/696,222 could be "fine tuned" by shifting their infra-red absorption peaks over small ranges (say 30 nm) in order to assist in providing dyes having absorptions within very narrow desired ranges.

It has now been found that providing an amino or substituted amino group in place of one of the oxygen atoms of the squarylium ring in squarylium dyes (the resulting dye being hereinafter referred to as an "aminosquarylium" dye) allows the absorption peak of the dye to be shifted somewhat, allows various functional groups to be incorporated conveniently into the dye, and may increase the solubility of the dye in, or its compatibility with, certain media. The amino group on the squarylium ring also provides a potential means for chemically bonding the dye to other materials. Accordingly, this invention is directed to these aminosquarylium dyes, to processes and intermediates for the preparation of such dyes, and to processes and imaging media containing these dyes.

SUMMARY OF THE INVENTION

This invention provides a squarylium compound of the formula:

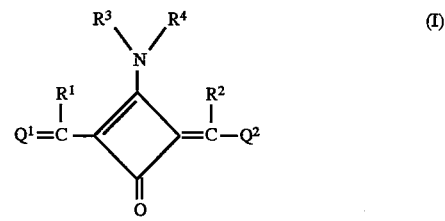

in which $Q^1$ and $Q^2$ are each a chromophoric group having an aromatic unsaturated system conjugated with the squarylium ring and such that in the compounds of formulae $Q^1CH_2R^1$ and $Q^2CH_2R^2$ the methylene hydrogens are active hydrogens, $R^1$ and $R^2$ are each independently a hydrogen atom or an aliphatic or cycloalkyl group, and $R^3$ and $R^4$ are each independently a hydrogen atom, or an acyl, aliphatic, cycloaliphatic, aromatic or heterocyclic group, subject to the proviso that one of $R^3$ and $R^4$ may be an amino or substituted amino group, or one of $R^3$ and $R^4$ is a hydrogen atom and the other is an organosulfonyl group, or $R^3$ and $R^4$ together with the intervening nitrogen atom form a nitrogenous heterocyclic ring.

The squarylium compounds of Formula I in which one of $R^3$ and $R^4$ is (notionally) a hydrogen atom and the other is an organosulfonyl group (i.e., in which a —SO$_2$NH— grouping is directly attached to the squarylium nucleus) (these compounds are typically encountered in their deprotonated form) can be synthesized in a manner which is different from that employed for the other squarylium compounds of Formula I, in that introduction of the sulfonamide group can be effected directly into the unsubstituted squarylium dye. Accordingly when hereinafter it is necessary to distinguish the two groups of compounds, the squarylium compounds of Formula I in which one of $R^3$ and $R^4$ is (notionally) a hydrogen atom and the other is an organosulfonyl group will be referred to as the "sulfonamide" compounds of Formula I, while the remaining compounds of Formula I will be referred to as the "non-sulfonamide" compounds. It should be noted that compounds of the present invention in which one of $R^3$ and $R^4$ is a sulfonated alkyl group are non-sulfonamide compounds.

This invention also provides a squaric acid derivative of the formula:

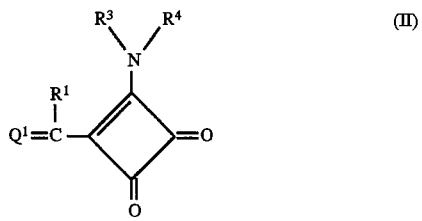

in which $Q^1$ is a chromophoric group having an aromatic unsaturated system conjugated with the squarylium ring and such that in the compound of formula $Q^1CH_2R^1$ the methylene hydrogens are active hydrogens, $R^1$ is a hydrogen atom or an aliphatic or cycloaliphatic group, and $R^3$ and $R^4$ are each independently a hydrogen atom, or an acyl, aliphatic, cycloaliphatic, aromatic or heterocyclic group, subject to the proviso that one of $R^3$ and $R^4$ may be an amino or substituted amino group, or $R^3$ and $R^4$ together with the intervening nitrogen atom form a nitrogenous heterocyclic ring.

This invention also provides a process for the preparation of a squaric acid derivative of Formula II, which process comprises reacting a corresponding squaric acid derivative of the formula:

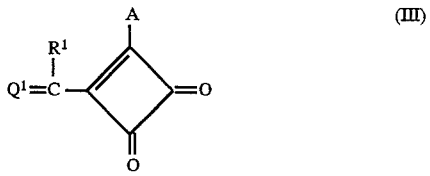

in which A is a chlorine or bromine atom, or an alkoxyl group, and $Q^1$ and $R^1$ are as defined above, with ammonia or a compound of formula $NHR^3$, $NHR^4$, or $NHR^3R^4$, in which $R^3$ and $R^4$ are as defined above. This process may hereinafter be referred to as the "first process of the invention".

This invention also provides a process for the preparation of a squarylium compound of Formula I above, which process comprises reacting a corresponding squaric acid derivative of Formula (II) above, in which $Q^1$, $R^1$, $R^3$ and $R^4$ are as defined above, with a compound of the formula $Q^2CH_2R^2$, in which $Q^2$ and $R^2$ are as defined above. This process may hereinafter be referred to as the "second process of the invention".

This invention also provides a process for the preparation of a sulfonamide squarylium compound of Formula I above, which process comprises reacting the corresponding squarylium compound of the formula:

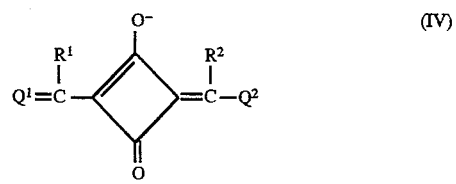

in which $Q^1$, $Q^2$, $R^1$ and $R^2$ are as defined above, with the corresponding organosulfonyl isocyanate. This process may hereinafter be referred to as the "third process of the invention".

This invention also provides a process for the preparation of a non-sulfonamide squarylium compound of Formula I above, which process comprises reacting a corresponding squaric acid monoester monoamide with at least one compound of formula $Q^1CH_2R^1$ or $Q^2CH_2R^2$. This process may hereinafter be referred to as the "fourth process of the invention".

This invention also provides a process for the preparation of a squaric acid derivative of Formula II above, which process comprises reacting a corresponding squaric acid monoester monoamide with a compound of formula $Q^1=CHR^1$. This process may hereinafter be referred to as the "fifth process of the invention".

This invention also provides a process for the preparation of a 1,3-disubstituted-2-amino or substituted amino squarylium dye, which process comprises reacting the corresponding 1,3-disubstituted-2-unsubstituted squarylium dye with an alkylating agent to produce a corresponding 1,3-disubstituted-2-alkoxy squarylium compound, and thereafter reacting the 2-alkoxy compound with ammonia or a primary or secondary amine to produce the 1,3-disubstituted-2-amino or substituted amino squarylium dye. This process may hereinafter be referred to as the "sixth process of the invention".

This invention also provides a compound of the formula:

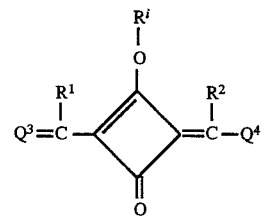

wherein $R^1$, $R^2$ and $R^i$ are each independently a hydrogen atom or an aliphatic or cycloaliphatic group, and $Q^3$ and $Q^4$ are each independently a pyrylium, thiopyrylium, selenopyrylium, benzpyrylium, benzthiopyrylium or benzselenopyrylium nucleus. These compounds may hereinafter be referred to as the "2-alkoxy compounds" of the present invention.

This invention also provides a process for generating heat in a medium comprising a dye of the present invention, which process comprises exposing at least part of the medium to infra-red actinic radiation of a frequency absorbed by the dye, whereby the radiation is absorbed by the dye and heat is generated within the parts of the medium exposed to the radiation.

Finally, this invention provides a thermal imaging medium comprising at least one imaging layer, the imaging layer comprising a color-forming compound which undergoes a change of color upon heating above a color-forming temperature for a color-forming time, the imaging layer further comprising a dye of the present invention.

It will be noted that the symbol $Q^1$ has been used for both a divalent grouping in Formulae I, II, III and IV, and a monovalent grouping in the formula $Q^1CH_2R^1$. This apparent anomaly is due to the fact that the bond orders in the compounds of Formula I, II, III and IV are not integral. For example, the dye A shown in FIG. 2 of the accompanying drawings is actually a resonance hybrid of the form shown and the similar form in which the positive charge resides on the oxygen atom of the other benzpyrylium nucleus (with contributions from other resonance forms). Thus, whether $Q^1$ is drawn as divalent or monovalent depends solely upon which of the contributing resonance forms is drawn, and similarly for $Q^2$. On the other hand, the compounds of formula $Q^1CH_2R^1$, such as the salt B shown in FIG. 1, are not resonance hybrids to any significant extent, and thus in this formula $Q^1$ is correctly shown as monovalent. The $Q^1/Q^2$ nomenclature employed will thus be clear to skilled chemists. Similar considerations apply to $Q^3$ and $Q^4$.

When either $R^3$ or $R^4$ in the compounds of Formulae I and II is hydrogen, the hydrogen atom(s) attached to the nitrogen are of course susceptible to being removed by bases, and the compounds may thus be encountered in deprotonated forms depending upon the pH of the medium containing the compound. Although the compounds of Formulae I and II are normally shown herein in their protonated forms, the invention extends to the deprotonated forms of these compounds. In particular, the sulfonamide compounds of Formula I are so readily deprotonated that they will often be found in their deprotonated form under neutral conditions. The discussion in the following four paragraphs assumes that the compounds of Formula I are present in their protonated form, but the consequences of deprotonation of the compound will readily be apparent to skilled chemists.

The compounds of Formula I produced by the processes of the present invention may be cationic, anionic or non-ionic. When none of the chromophoric groups $Q^1$ and $Q^2$ and the substituents $R^1$, $R^2$, $R^3$ and $R^4$ carries any charged substituents, the $Q^1Q^2$-aminosquarate moiety (hereinafter referred to simply as the "dye moiety") bears a single positive charge, and hence the dye is cationic. However, any one or more of the chromophoric groups $Q^1$ and $Q^2$ and the substituents $R^1$, $R^2$, $R^3$ and $R^4$ may carry a negatively or positively charged group (for example a —COO⁻ or trialkylammonium substituent), and if one or more negatively charged substituents is present, the dye will be non-ionic or anionic respectively.

When a counterion is present in a cationic or anionic dye of the present invention, the counterion may be any counterion which is not incompatible with the dye moiety and which thus provides a stable salt. The choice of counterion may be important in ensuring the solubility of the dye in various media, and reducing or preventing aggregation of the dye; minimizing aggregation of the dye is highly desirable since such aggregation can significantly reduce the apparent extinction coefficient of the dye in polymeric media.

Similarly, if the chromophoric group $Q^1$ or $Q^1$ does not carry any charged substituents (such nuclei being generally preferred in the present processes), the "compounds" $Q^1CH_2R^1$ and $Q^2CH_2R^2$ used in the present processes are actually cations. The counterion present may be any counterion which provides a stable salt and which does not interfere with the relevant reactions. Typically, large fluorinated anions, such as trifluoromethane sulfonate and tetrafluoroborate have been found to give good results in the present processes. The groups $Q^1$ and $Q^2$ may; however, bear charged substituents and thus in some cases $Q^1CH_2R^1$ and $Q^2CH_2R^2$ may be neutral compounds which do not require the presence of a counterion.

It may often be found convenient, for synthetic reasons, to prepare a desired moiety with one counterion and thereafter to effect a counterion exchange to form a different salt of the same moiety. Methods for such counterion ion exchange are well known to those skilled in the art.

DETAILED DESCRIPTION OF THE INVENTION

Figure 1:
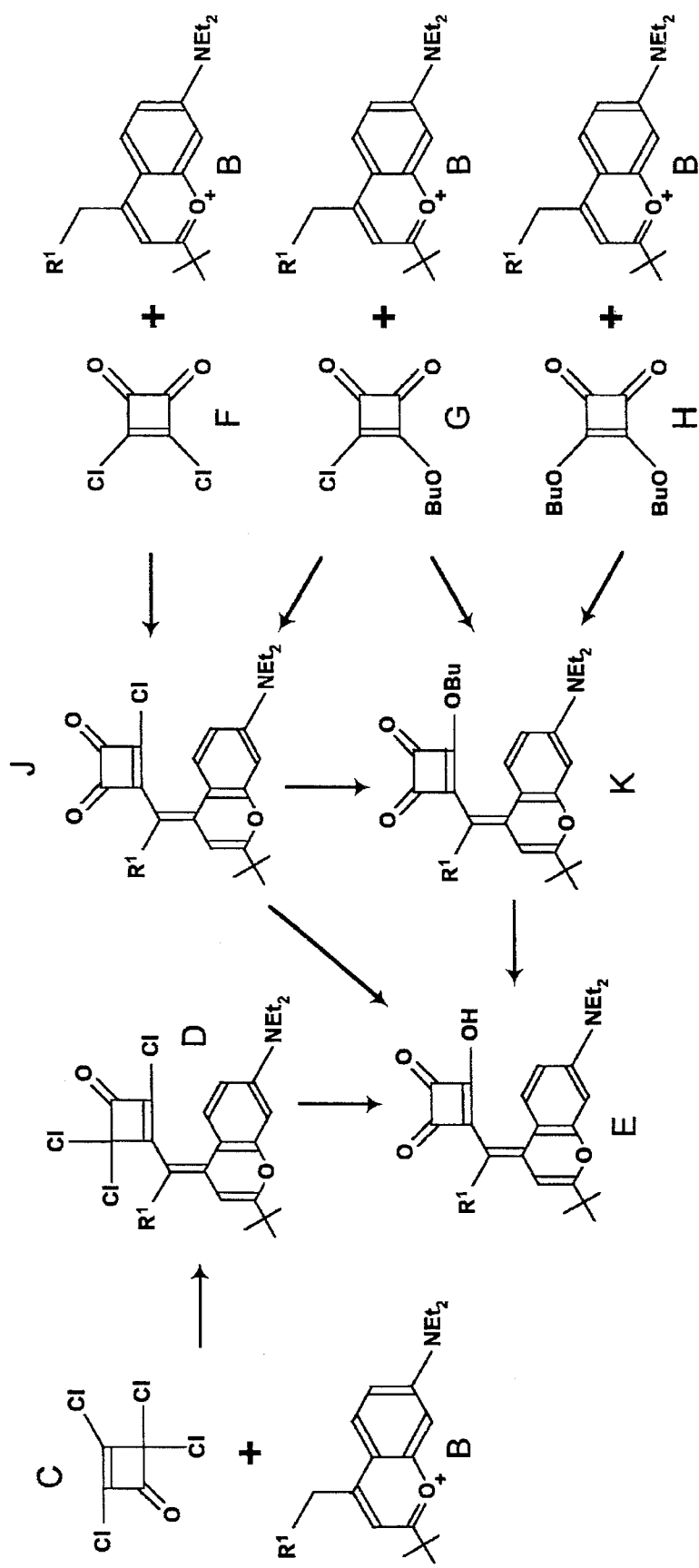
FIG. 1 of the accompanying drawings shows a synthetic scheme for the preparation of a starting material of Formula III used in the present invention by reactions described in the aforementioned application U.S. Ser. No. 07/696,222.
Figure 2:
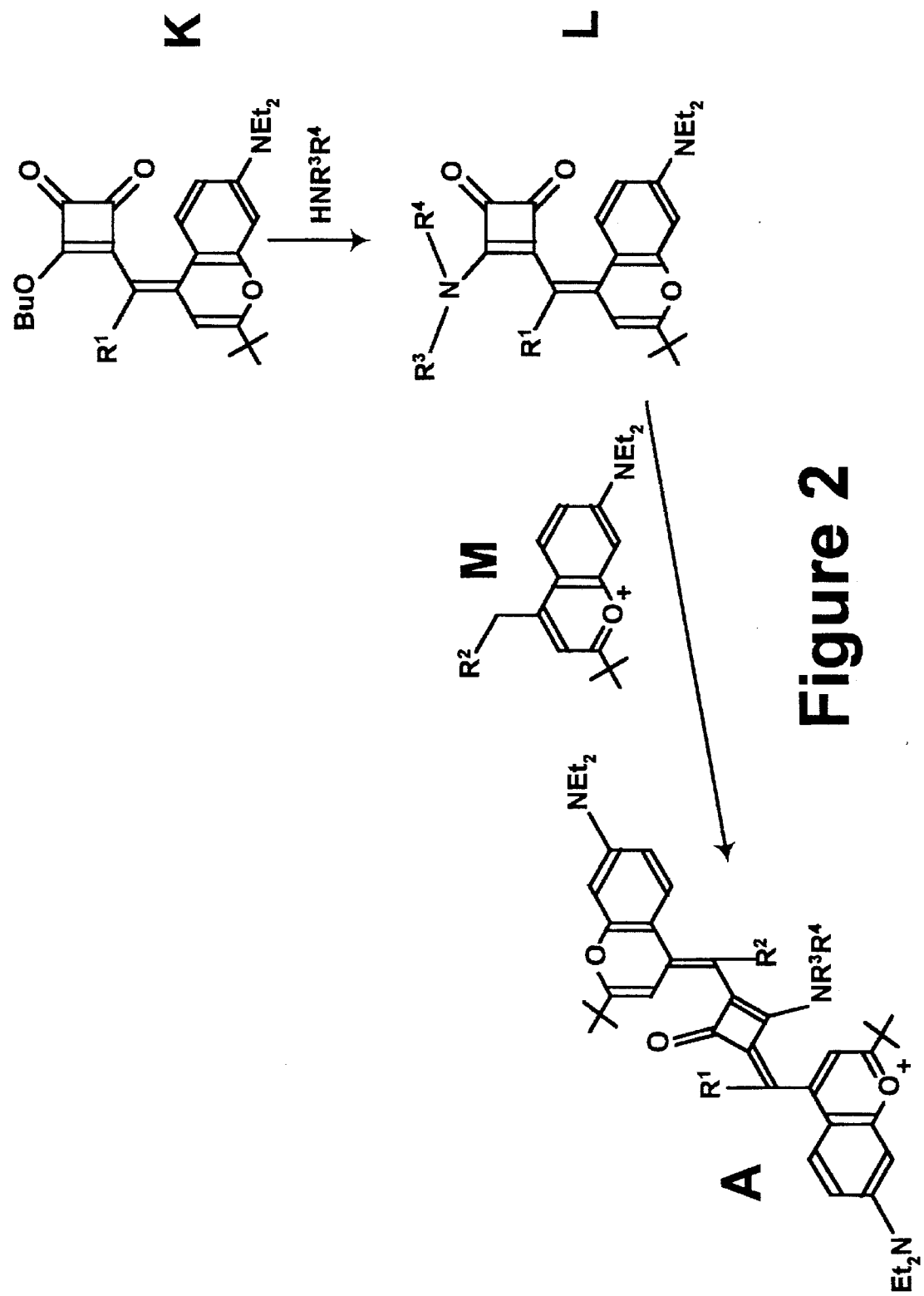
FIG. 2 shows the conversion of a starting material of Formula III to a squaric acid derivative of Formula II and thence to a squarylium compound of Formula I by the first and second processes of the present invention.

The interrelationships among the various reactions of the present invention may best be seen from the accompanying drawings. FIGS. 1 and 2 show a synthetic scheme for the preparation of a squarylium compound (hereinafter referred to as "Dye A") of Formula I, in which $Q^1$ is (in the resonance hybrid drawn) a 7-diethylamino-2-(1,1-dimethylethyl)-(benz[b]-4H-pyran-4-ylidene) grouping and $Q^2$ is a 4-[7-diethylamino-2-(1,1-dimethylethyl)-benz[b]pyrylium] grouping. The reactions shown in FIG. 1 are described in the aforementioned application U.S. Ser. No. 07/696,222, while the reactions shown in FIG. 2 are examples of the first and second processes of the present invention. Accordingly, the reactions shown in FIG. 1 will only be briefly described herein, and for fuller details the reader is referred to the copending application U.S. Ser. No. 07/696,222.

One form of the synthesis begins with the condensation of a 2,6-bis-(1,1-dimethylethyl)-4-($R^1$-methyl)-7-diethylaminobenzpyrylium salt B (a compound of Formula $Q^1CH_2R^1$) with 2,3,4,4-tetrachlorocyclobut-1-en-2-one C to give the trihalosquaric acid derivative D. The tetrachloro compound C and its synthesis are described in Maahs et al., "Syntheses and Derivatives of Squaric Acid", Angew. Chem. Int. Ed., 5, 888–893 (1966). This reaction is conducted in the presence of a base, preferably triethylamine. As noted above, the anion of the salt B can be any anion which provides a stable salt and which does not interfere with the desired reaction; conveniently the tetrafluoroborate salt is used.

As may be seen from FIGS. 1 and 2, use of the 4-methylbenzpyrylium salt B ($R^1$ is a hydrogen atom) will produce a dye in which $R^1$ is hydrogen. If the 4-methyl group of the salt B is replaced with a different group of the formula —$CH_2R^1$, the corresponding dyes can be produced in which $R^1$ is an aliphatic or cycloaliphatic group; thus, for example, the use of a 4-ethyl salt gives a final dye in which $R^1$ is methyl. Similar variations in the group $R^2$ may be produced by varying the 4-substituent in the benzpyrylium salt of Formula M (described below). The tetrabromo homologue may be used in place of the tetrachloro compound C.

In the next step of the synthesis, the trihalosquaric acid derivative D is hydrolyzed to the corresponding non-halogenated derivative E. Desirably, this hydrolysis is effected by heating the derivative D with triflic acid, then adding water.

Alternatively, the non-halogenated derivative E may be prepared by condensing the salt B with the diacid chloride (F), an ester/acid chloride (G) or a diester (H) of squaric acid (the butyl ester/acid chloride and diester are shown in FIG. 1), followed by hydrolysis of the resultant product. With both the monoacid chloride/monoester G and the diester H, this reaction requires the presence of a base to produce useful yields; with the more reactive diacid chloride F, this reaction can be conducted without base. The reaction of the diacid chloride F may also be promoted by a Lewis acid.

When the diacid chloride F is used as starting material in this reaction, the intermediate is J, the acid chloride of E, whereas when the diester H is used as starting material, the intermediate is K, the ester of E. When the ester/acid chloride G is used, both J and K are produced, but the production of this mixture poses no problems, since both compounds are readily hydrolyzed to give the derivative E. If desired, the add chloride J may be treated with methanol to convert it to the ester K. Add bromides may be used in place of the acid chlorides, and the group $R^1$ may be varied by changing the 4-substituent on the salt B, as described above.

In FIG. 2 there is shown the first process of the invention, namely the reaction of the ester K with a nitrogen compound of formula $HNR^3R^4$ to produce the corresponding amino squaric acid derivative L. Although the ester K has been shown in FIG. 2, this reaction may also be conducted using the acid chloride J shown in FIG. 1.

The final step of the synthesis of the squarylium dye A is an example of the second process of the present invention, namely the condensation of the squaric acid derivative L with one mole of the appropriate compound of formula $Q^2CH_2R^2$; the compound in which $Q^2$ is a 2-(1,1-dimethylethyl)-7-diethylaminobenzpyrylium group is shown in FIG. 2. The conditions required for this reaction may be substantially the same as those used for the prior art reactions in which two moles of a benzpyrylium salt are condensed with squaric acid to form a symmetric bisbenzpyrylium dye. Thus, this reaction is assisted by base, conveniently a tertiary amine, for example quinoline. The reaction is desirably conducted in solution in an alcohol, conveniently butanol. Alternatively, this reaction may be promoted by a Lewis acid, for example a titanium tetrahalide, conveniently in dichloromethane.

Although the reaction L→A illustrated in FIG. 2 produces a dye A in which $Q^1$ is the same as $Q^2$, it will readily be apparent that this need not be the case, since the group $Q^1$ derived from compound B (FIG. 1) could be different from the group $Q^2$ derived from compound M. Thus, the synthesis shown in FIGS. 1 and 2 can be used to produce both symmetric dyes, in which $Q^1$ and $Q^2$ are the same, and asymmetric dyes in which these two groups are different.

In many cases, the synthesis of the final aminosquarylium dye is most simply achieved by introducing the final $NR^3R^4$ group during the preparation of the compound L; for example, when each of $R^3$ and $R^4$ is a hydrogen atom or an alkyl group, so that the compound $HNR^3R^4$ is ammonia or a primary or secondary amine, the reaction K→L proceeds well with ammonia or a primary or secondary amine so that there is no difficulty in incorporating the final $NR^3R^4$ group in this step of the synthesis. However, in other cases, the substituents $R^3$ and $R^4$ may be such that they interfere with the reaction L→A. In such circumstances it is preferred to use a different compound $HNR^3R^4$ in the reaction K→L, and then to modify $R^3$ and/or $R^4$ in the final dye A. For example, as illustrated in Example 21 below, if one of $R^3$ and $R^4$ is to be a hydrogen atom and the other an acyl group, it is convenient to carry out the reaction K→L with ammonia, thereby producing an intermediate L and a dye A in which both $R^3$ and $R^4$ are hydrogen atoms, and then to react this dye A with the appropriate acyl chloride (or other acyl halide) to attach the desired acyl group to the amine substituent.

Furthermore, as discussed in more detail below, the groups $R^3$ and $R^4$ may contain various functional groups, and some of these functional groups may be capable of interfering with one or both of the reactions K→L and L→A. For example, the reaction L→A depends upon the presence of active hydrogens in the compound $Q^2CH_2R^2$, and any functional groups within the groups $R^3$ and $R^4$ which contain active hydrogens may interfere with this reaction. In such cases, it may be necessary to modify the synthesis shown in FIG. 2 either by modifying the group $R^3$ and/or $R^4$ in the dye A (in the same manner as discussed above for the case where $R^3$ or $R^4$ is an acyl group), or by blocking the functional groups in the compound $HNR^3R^4$ and then unblocking these groups in the dye A.

Figure 3:
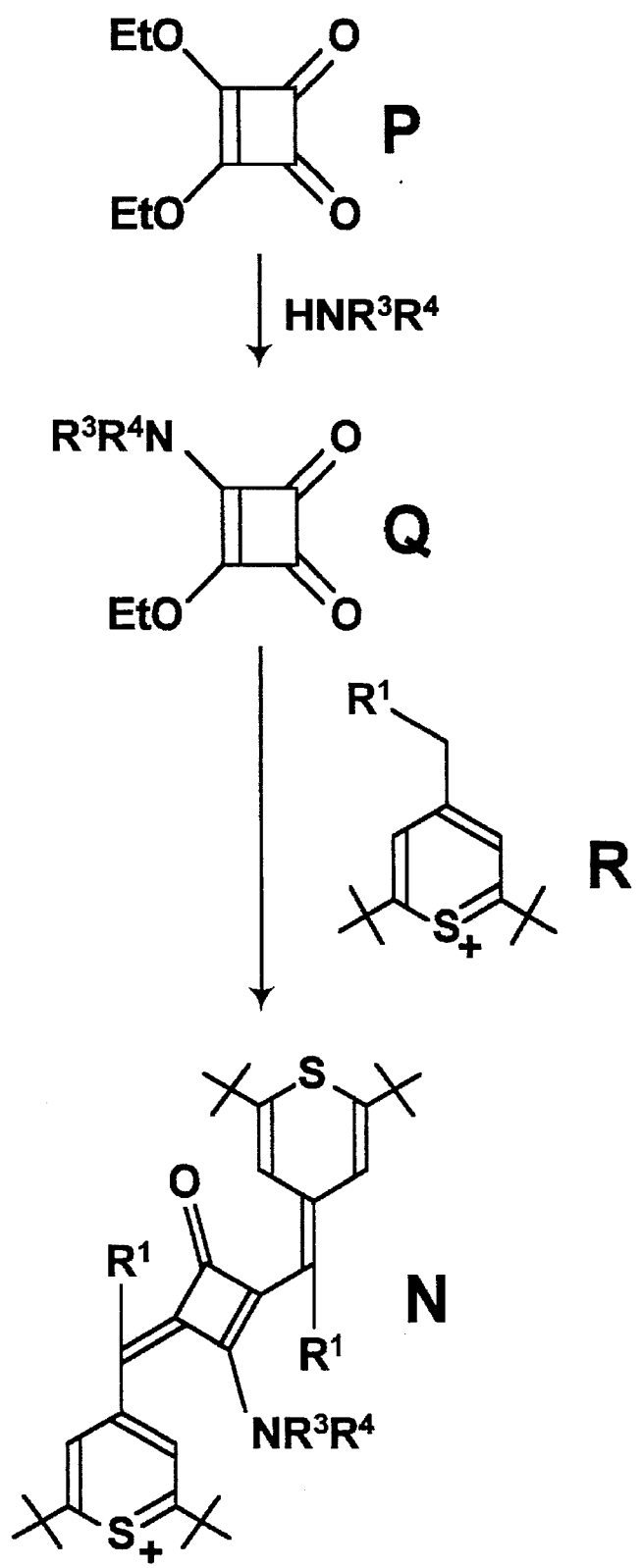
FIG. 3 shows the synthesis of a squarylium compound of Formula I from a corresponding squaric acid monoester monoamide by the fourth process of the present invention.

FIG. 3 shows an alternative synthesis of a dye N starting from a diester P of squaric acid (the diethyl ester is illustrated in FIG. 3) and using the fourth reaction of the present invention. The diester P is first condensed with a compound of formula $HNR^3R^4$ to introduce an amino group, thereby producing the corresponding squaric acid monoester monoamide Q, which is then condensed with two moles of a compound R of formula $Q^1CH_2R^1$ (the salt in which $Q^1$ is a 2,6-bis(1,1-dimethylethyl)thiopyrylium group is illustrated in FIG. 3) to produce the final symmetrical dye N. The reaction Q→N may be carried out under the same conditions as the reaction L→A described above with reference to FIG. 2. Also, the synthesis shown in FIG. 3 may be modified to include changes in the group $R^3$ and/or $R^4$ in the dye N, and the blocking of functional groups, as discussed above with reference to FIG. 2.

At present, the synthetic route shown in FIG. 2 is preferred over that shown in FIG. 3 because the former tends to give better yields of dye and because the former is capable of producing asymmetric dyes in good yield. (Although theoretically the synthesis shown in FIG. 3 might be modified to produce asymmetric dyes by treating the monoester monoamide Q with a mixture of two different compounds $Q^1CH_2R^1$ and $Q^2CH_2R^2$, this approach is not recommended, since the separation of the resultant mixture of three dyes (two symmetric dyes and the desired asymmetric dye) is likely to be very difficult.)

Figure 4:
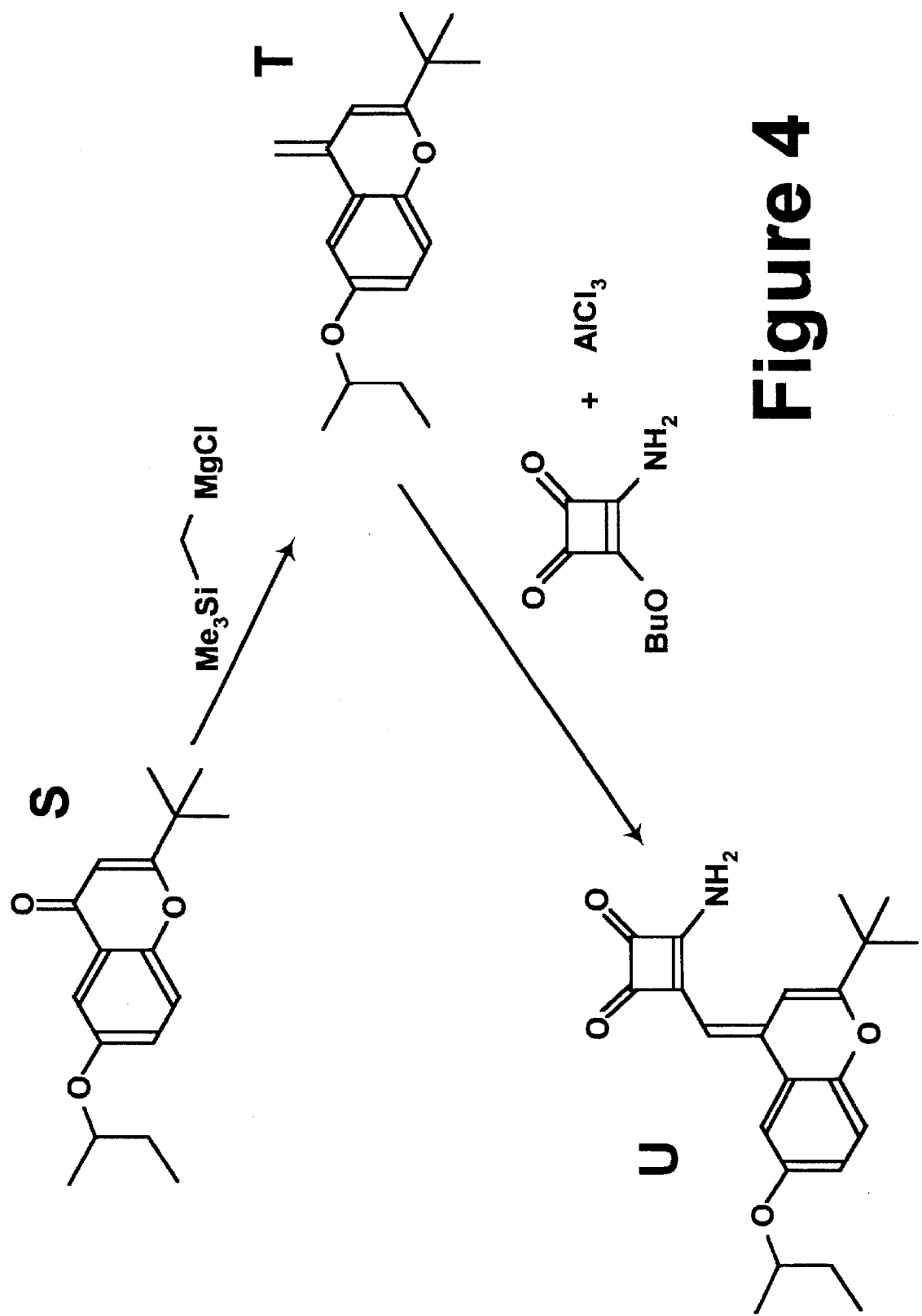
FIG. 4 shows the preparation of an exo-alkylene compound of the present invention by the fifth process of the present invention, and the condensation of this exo-alkylene compound with a squaric acid monoester monoamide to produce the same type of intermediate as shown in FIGS. 2 and 3.

FIG. 4 illustrates the preparation of an intermediate U, which is analogous to the intermediate L shown in FIG. 2, by a synthetic route which exemplifies the fifth process of the present invention and proceeds via an exo-alkylene compound. The synthesis shown in FIG. 4 begins from a chromone S; this chromone can be prepared by a variety of processes known to persons skilled in the art of organic synthesis. Certain methods for the synthesis of such chromones are exemplified below, and other are described in the aforementioned copending applications Ser. Nos. 07/616,639 and 07/795,038. The chromone S is first converted to the corresponding exo-methylene compound T by means of a Peterson olefination, as described in, for example, Organic Reactions, Vol. 38, 1–225 (Wiley, New York, 1990); alternatively the exo-methylene compound may be produced by treating the corresponding compound of formula $Q^1CH_2R^1$ with a strong base. The exo-methylene compound T is then reacted with a squaric acid monoester monoamide to produce the intermediate S; this reaction is somewhat analogous to the reaction Q+R→N shown in FIG. 3, but only monocondensation occurs, so that the intermediate S is analogous to the intermediate L shown in FIG. 2. The conversion of T to U is desirably catalyzed by a Lewis acid, preferably an aluminum halide such as aluminum chloride. It will readily be apparent that the intermediate L can readily be converted to a dye of the present invention by a reaction analogous to L+M→A shown in FIG. 2.

In at least some cases, the dyes of Formula I cannot be synthesized by reacting the corresponding dye having an unsubstituted squarylium nucleus with an amino compound, since in these cases the amino compound simply adds reversibly to the squarylium dye. However, unsubstituted squarylium dyes can be converted to aminosquarylium dyes of the present invention by the indirect route shown in FIG. 5, which illustrates the sixth process of the present invention. In this indirect route, an unsubstituted squarylium dye V is first treated with an alkylating agent, preferably a dialkyl sulfate, to produce the corresponding 2-alkoxysquarylium compound W, and this 2-alkoxy compound is then treated with a compound of formula $HNR^3R^4$ (typically ammonia or a primary or secondary amine; butylamine is shown for purposes of illustration in FIG. 5) to produce the final aminosquarylium dye.

The syntheses shown in FIGS. 2–5 are primarily intended for preparing non-sulfonamide dyes of the present invention. The sulfonamide dyes of the present invention are conveniently synthesized by treating the corresponding squarylium dye with the appropriate organosulfonyl isocyanate, with elimination of carbon dioxide; for example tosyl isocyanate ($p\text{-}CH_3\text{---}C_6H_4\text{---}SO_2NCO$) converts a squarylium dye to the corresponding p-tolylsulfonamido squarylium dye. This reaction proceeds readily in solution in a non-polar solvent, for example toluene, no catalyst being required. The reaction is not confined to aromatic sulfonyl isocyanates and can be carried out with alkyl sulfonyl isocyanates, for example butylsulfonyl isocyanate.

As already indicated, a wide range of groups $R^3$ and $R^4$ can be present in the squarylium dyes of the present invention. Thus, for example, $R^3$ and $R^4$ can each independently be a hydrogen atom or an acyl, aliphatic, cycloaliphatic, aromatic or heterocyclic group, subject to the proviso that one of $R^3$ and $R^4$ may be an amino or substituted amino group, or one of $R^3$ and $R^4$ can be a hydrogen atom and the other be an organosulfonyl group, such as a tosylsulfonyl group. For example, $R^3$ and $R^4$ can each be an alkyl, alkenyl, alkynyl, cycloalkyl (for example, a cyclohexyl group) or cycloalkenyl group, a polycyclic saturated group such as a decalinyl or adamantyl group, or a similar group containing ethylenic unsaturation (for example a 6,6-dimethylbicyclo[3.1.1.]hept-2-en-2-yl or bicyclo[2.2.1]hept-2-en-5-yl group) an aromatic group (for example, a phenyl group), or a saturated or unsaturated heterocyclic group (for example, a piperidino group). In addition, $R^3$ and $R^4$, together with the intervening nitrogen atom, may form a nitrogenous heterocyclic ring; thus, for example, the $NR^3R^4$ grouping could be a piperidino or indolino group, and may contain additional hetero atoms, as for example in a morpholino or pyrimidino group. One of $R^3$ and $R^4$ can also be an amino or substituted (for example, alkyl or cycloalkyl substituted) amino group, so that the $NR^3R^4$ grouping may be a substituted or unsubstituted hydrazine grouping, for example a trimethylhydrazine grouping.

Any of these groups $R^3$ and $R^4$ may be unsubstituted or substituted; as indicated above, it is one of the advantages of the dyes of the present invention that the nitrogen on the squarylium ring, and the groups $R^3$ and $R^4$ attached thereto, provide convenient sites to which a variety of groups may be attached in order to modify the properties of the dye, without having to change the chromophoric groups $Q^1$ and $Q^2$. Thus, the groups $R^3$ and $R^4$ may contain substituents which affect the solubility of the dye in various media. For example, if it desired to increase the solubility of the dye in highly polar solvents, the groups $R^3$ and $R^4$ may contain sulfonic acid, carboxyl or quaternary ammonium groups. On the other hand, if it desired to increase the solubility of the dye in non-polar solvents, the groups $R^3$ and $R^4$ may be unsubstituted long-chain alkyl groups. The groups $R^3$ and $R^4$ may also contain substituents such as halo, cyano, amino, oxo and phenyl groups, ether, amide and urethane linkages.

The groups $R^3$ and $R^4$ may also contain groups which permit linking the dye to other materials, thereby permitting, for example, the dye to be incorporated into a polymer.

The groups $R^3$ and $R^4$ also affect the spectrum of the squarylium dye. In general, the wavelength ($\lambda_{max}$) of maximum absorption of the dye in the near infra-red becomes longer as the groups $R^3$ and $R^4$ become more electron donating. For example, in the dyes A shown in FIG. 2, the variation of $\lambda_{max}$ with changes in the $NR^3R^4$ group is as follows:

| $NR^3R^4$ | $\lambda_{max}$, nm |
|---|---|
| $NH_2$ | 797 |
| $NHCH_2CH_2SO_3^-$ | 810 |
| $N(C_2H_5)_2$ | 828 |

The corresponding unsubstituted squarylium dye, in which the group $NR^3R^4$ is replaced by $O^-$, has $\lambda_{max}$=808 nm. Thus, in this series of dyes, modification of the unsubstituted squarylium dye by incorporation of these amino groups permits modification ("fine tuning") of $\lambda_{max}$ over a range of −11 to +20 nm.

The value of $\lambda_{max}$ is also affected by deprotonation of the dye. As mentioned above, if $R^3$ and/or $R^4$ in Formula I is a hydrogen atom, this hydrogen atom may be removed by bases. As shown in Example 54 below, such deprotonation of the dye typically shifts $\lambda_{max}$ about 60 nm longer. Thus, in cases where it is desired to provide absorption at longer wavelengths, it may be advantageous to incorporate a dye of the present invention in a basic medium, either by using a basic binder in such a medium or by providing a separate base in the medium, such that the dye exists in the medium in its deprotonated form.

Although the invention has been shown in the accompanying drawings and described above with reference to compounds in which $Q^1$ and $Q^2$ are each a pyrylium or benzpyrylium nucleus, it will be apparent that both $Q^1$ and $Q^2$ can each independently be any chromophoric group such that in the compounds of formulae $Q^1CH_2R^1$ and $Q^2CH_2R^2$ the methylene hydrogens are active hydrogens, so that these methylene hydrogen atoms can undergo the condensations with squaric acid derivatives already described. It is preferred that the atoms of $Q^1$ and $Q^2$ which are bonded directly to the $CR^1$ and $CR^2$ groupings respectively each be part of an aromatic ring. For example, $Q^1$ and $Q^2$ may each independently be an imidazole, benzimidazole, thiazole, benzthiazole, oxazole, benzoxazole, 2- or 4-pyridinium, 2- or 4-quinolinium or indolinium nuclei. Desirably, at least one, and preferably both, of $Q^1$ and $Q^2$ is a non-nitrogenous heterocyclic nucleus, especially preferred nuclei being pyrylium, thiopyrylium, selenopyrylium, benzpyrylium, benzthiopyrylium and benzselenopyrylium nuclei. Such nuclei be either the 2- or 4-isomers, although the latter are preferred.

In one preferred group of dyes of Formula I, $Q^1$ and/or $Q^2$ is a 2,6-dialkylpyrylium, -thiopyrylium or -selenopyrylium nucleus, in which each of the alkyl groups contains not more than about 8 carbon atoms, especially those in which $Q^1$ and/or $Q^2$ is a 2,6-di-tertiary butylpyrylium, -thiopyrylium or -selenopyrylium nucleus. The presence of these nuclei in the dyes has been found to provide good solubility in polymeric media and high extinction coefficients.

Another preferred group of dyes of Formula I are those in which $Q^1$ and/or $Q^2$ is a 4-benzpyrylium, 4-benzthiopyrylium or 4-benzselenopyrylium nucleus, desirably such a nucleus which carries at its 2-position a substituent in which a non-aromatic carbon atom is bonded directly to the benzpyrylium nucleus, subject to the proviso that if this 2-substituent contains an aromatic nucleus, this aromatic nucleus is not conjugated with the benzpyrylium nucleus. The 2-substituent may be, for example:

a. an alkyl group, for example an isopropyl, sec-butyl, tert-butyl, 2-ethyl-2-methylbutyl or 2,2-dimethylbutyl group;

b. an alkenyl group, for example a vinyl group;

c. an alkynyl group, for example an ethine group;

d. a cycloalkyl group, for example a cyclohexyl group;

e. a cycloalkenyl group, for example a cyclohexenyl group;

f. a polycyclic saturated hydrocarbon group, for example a decalinyl or adamantyl group;

g. a polycyclic, ethylenically unsaturated hydrocarbon group, for example a 6,6-dimethylbicyclo[3.1.1]hept-2-en-2-yl or bicyclo[2.2.1]hept-2-en-5-yl group;

h. any of the foregoing substituents substituted with aryl, halo, cyano, amino or oxo groups, or containing ether, amine or urethane linkages. The 2-substituent is desirably one in which the carbon atom which is directly attached to the benzpyrylium nucleus carries not more than one hydrogen atom.

The benzpyrylium nucleus may also carry at its 7-position a substituent in which an element of Group 5A, 6A or 7A of the Periodic Table is directly connected to the benzpyrylium nucleus, subject to the proviso that when this element of Group 5A or 6A, the 7-substituent may be at least one saturated ring containing this element of Group 5A or 6A, this saturated ring optionally being fused to the phenyl ring of the associated benzpyrylium nucleus. Preferred 7-substituents are alkoxy groups containing not more than about 12 carbon atoms, or disubstituted amine or disubstituted phosphino groups, wherein each of the substituents on the or each disubstituted group comprises an alkyl group containing not more than about 6 carbon atoms, or the two substituents on any one disubstituted group together form, with the nitrogen or phosphorus atom thereof, a heterocyclic ring system, this ring system optionally being fused to the benzpyrylium nucleus which carries the disubstituted amine or phosphino substituent. Examples of suitable 7-substituents include dialkylamino wherein each of the alkyl groups contains not more than about 4 carbon atoms, piperidino, indolinyl, morpholino and —N[—$(CH_2)_3$—]$_2$ groups, subject to the proviso that when one or both of the amine groups is a —N[—$(CH_2)_3$—]$_2$ group, the ends of the trimethylene groups remote from the nitrogen atom are joined to the 6- and 8-positions of the benzpyrylium nucleus carrying the nitrogen atom, so that the —N[—$(CH_2)_3$—]$_2$ group and the benzene ring of the benzpyrylium nucleus together form a julolidine ring system. As described in the aforementioned applications U.S. Ser. Nos. 07/616,639 and 07/795,038, dyes containing such 4-benzpyrylium nuclei have desirable properties, including solubility in polymeric media and high extinction coefficients.

Alternatively, the or each benzpyrylium nucleus may carry at its 6-position an alkoxy, alkenyloxy or alicyclyloxy group; the alkyl, cycloalkyl or alicyclic portion of this group may be any of the groups (other than alkynyl) mentioned above as the 2-substituent. Desirably the 6-substituent is an alkoxy or cycloalkoxy group, preferably a branched chain alkoxy group. Specific preferred branched chain alkoxy groups are propoxy, but-2-oxy and 2-ethylbutoxy groups. Preferably, the benzene ring of the benzpyrylium nucleus bears no substituents other than the 6-substituent. It has been found that providing such a branched-chain 6-substituent increases the solubility of the dye in polymeric media. In addition, such 6-substituted dyes tend to have relatively low visible extinction and are thus advantageous for use in applications (such as thermal imaging media) where visible absorption is undesirable. It is believed (although the invention is in no way limited by this belief) that the advantageous solubility properties of the aforementioned 6-substituted dyes are due at least in part to the 6-substituent extending out of the plane of the aromatic nucleus to which it is attached, and thus the choice of a 6-substituent may be influenced by the stereochemistry of the substituent, not merely its chemical nature.

Although $R^1$ and $R^2$ may be other groups, for example cycloalkyl groups or any of the other aliphatic and cycloaliphatic groups discussed above as potential 2-substituents on benzpyrylium groups $Q^1$ and $Q^2$, it is preferred that these two groups each independently be a hydrogen atom or an alkyl group containing not more than about 6 carbon atoms.

Specific preferred dyes of Formula I are those in which:

a. $Q^1$ is a 2-(1,1-dimethylethyl)-7-diethylaminobenz[b]-4H-pyran-4-ylidene grouping, $Q^2$ is a 4-[2-(1,1-dimethylethyl)-7-diethylaminobenz[b]-4H-pyrylium] grouping, and $R^1$, $R^2$, $R^3$ and $R^4$ are each a hydrogen atom, namely, a 4-[[2-amino-3-[[7-diethylamino-2-[1,1-dimethylethyl]benz[b]-4H-pyran-4-ylidene]methyl]-4-oxo-2-cyclobuten-1-ylidene]methyl]-7-diethylamino-2-[1,1-dimethylethyl]benz[b]pyrylium salt;

b. $Q^1$ is a 2-(1,1-dimethylethyl)-7-diethylaminobenz[b]-4H-pyran-4-ylidene grouping, $Q^2$ is a 4-[2-(1,1-dimethylethyl)-7-diethylaminobenz[b]-4H-pyrylium] grouping, $R^3$ and $R^4$ are each an ethyl group and $R^1$ and $R^2$ are each a hydrogen atom, namely a 4-[[2-diethylamino-3-[[7-diethylamino-2-[1,1-dimethylethyl]benz[b]-4H-pyran-4-ylidene]methyl]-4-oxo-2-cyclobuten-1-ylidene]methyl]-7-diethylamino-2-[1,1-dimethylethyl]benz[b]pyrylium salt;

c. $Q^1$ is a 2-(1,1-dimethylethyl)-7-diethylaminobenz[b]-4H-pyran-4-ylidene grouping, $Q^1$ is a 4-[2-(1,1- dimethylethyl)-7-diethylaminobenz[b]-4H-pyrylium] grouping, $R^3$ is a butyl group and $R^1$, $R^2$ and $R^4$ are each a hydrogen atom, namely a 4-[[2-butylamino-3-[[7-diethylamino-2-[1,1-dimethylethyl]benz[b]-4H-pyran-4-ylidene]methyl]-4-oxo-2-cyclobuten-1-ylidene]methyl]-7-diethylamino-2-[1,1-dimethylethyl]benz[b]pyrylium salt;

d. $Q^1$ is a 2-(1,1-dimethylethyl)-7-diethylaminobenz[b]-4H-pyran-4-ylidene grouping, $Q^2$ is a 4-[2-(1,1-dimethylethyl)-7-diethylaminobenz[b]-4H-pyrylium] grouping, $R^3$ is a —$CH_2CH_2SO_3H$ grouping, and $R^1$, $R^2$ and $R^4$ are each a hydrogen atom, namely the 4-[[2-[3-sulfonatoprop-1-ylamino]-3-[[7-diethylamino-2-[1,1-dimethylethyl]benz[b]-4H-pyran-4-ylidene]methyl]-4-oxo-2-cyclobuten-1-ylidene]methyl]-7-diethylamino-2-[1,1-dimethylethyl]benz[b]pyrylium inner salt;

e. $Q^1$ is a 2-(1,1-dimethylethyl)-7-diethylaminobenz[b]-4H-pyran-4-ylidene grouping, $Q^2$ is a 4-[2-(1,1-dimethylethyl)-7-diethylaminobenz[b]-4H-pyrylium] grouping, $R^3$ is a pivaloyl grouping and $R^1$, $R^2$ and $R^4$ are each a hydrogen atom, namely a 4-[[3-[[7-diethylamino-2-[1,1-dimethylethyl]benz[b]-4H-pyran-4-ylidene]methyl]-4-oxo-2-pivaloylamino-2-cyclobuten-1-ylidene]methyl]-7-diethylamino-2-[1,1-dimethylethyl]benz[b]pyrylium salt;

f. $Q^1$ is a 2,6-bis(1,1-dimethylethyl)-4H-thiopyran-4-ylidene grouping, $Q^2$ is a 4-[2,6-bis(1,1-dimethylethyl)-4H-thiopyrylium] grouping, and $R^1$, $R^2$, $R^3$ and $R^4$ are each a hydrogen atom, namely a 4-[[2-amino-3-[[2,6-bis-[1,1-dimethylethyl]thio-4H-pyran-4-ylidene]methyl]-4-oxo-2-cyclobuten-1-ylidene]methyl]-2,6-bis-[1,1-dimethylethyl]thiopyrylium salt;

g. $Q^1$ is a 2,6-bis(1,1-dimethylethyl)-4H-thiopyran-4-ylidene grouping, $Q^2$ is a 4-[2,6-bis(1,1-dimethylethyl)-4H-thiopyrylium] grouping, $R^1$ is a methyl group, and $R^2$, $R^3$ and $R^4$ are each a hydrogen atom, namely a 4-[[2-amino-3-[1-[2,6-bis[1,1-dimethylethyl]thio-4H-pyran-4-ylidene]-eth-1-yl]-4-oxo-2-cyclobuten-1-ylidene]methyl]-2,6-bis[1,1-dimethylethyl]thiopyrylium salt;

h. $Q^1$ is a 2,6-bis(1,1-dimethylethyl)-4H-thiopyran-4-ylidene grouping, $Q^2$ is a 4-[2,6-bis(1,1-dimethylethyl)-4H-thiopyrylium] grouping, $R^3$ is a $CH_3CH_2CH_2CH_2SO_2$— grouping, and $R^1$, $R^2$ and $R^4$ are each a hydrogen atom, namely the 4-[[3-[[2,6-bis[1,1-dimethylethyl]thio-4H-pyran-4-ylidene]methyl]-2-butanesulfonylamino-4-oxo-2-cyclobuten-1-ylidene]methyl]-2,6-bis[1,1-dimethylethyl]thiopyrylium hydroxide inner salt;

i. $Q^1$ is a 2,6-bis(1,1-dimethylethyl)-4H-thiopyran-4-ylidene grouping, $Q^2$ is a 4-[2,6-bis(1,1-dimethylethyl)-4H-thiopyrylium] grouping, $R^3$ is a butyl group and $R^1$, $R^2$ and $R^4$ are each a hydrogen atom, namely a 4-[[2-butylamino-3-[[2,6-bis[1,1-dimethylethyl]thiopyran-4-ylidene]methyl]-4-oxo-2-cyclobuten-1-ylidene]methyl]-2,6-bis[1,1-dimethylethyl]thiopyrylium salt;

j. $Q^1$ is a 2,6-bis(1,1-dimethylethyl)-4H-selenopyran-4-ylidene grouping, $Q^2$ is a 4-[2,6-bis(1,1-dimethylethyl)-4H-selenopyrylium] grouping, and $R^1$, $R^2$, $R^3$ and $R^4$ are each a hydrogen atom, namely a 4-[[2-amino-3-[[2,6-bis-[1,1-dimethylethyl]seleno-4H-pyran-4-ylidene]methyl]-4-oxo-2-cyclobuten-1-ylidene]methyl]-2,6-bis[1,1-dimethylethyl]selenopyrylium salt;

k. $Q^1$ is a 2,6-bis(1,1-dimethylethyl)-4H-selenopyran-4-ylidene grouping, $Q^2$ is a 4-[2,6-bis(1,1-dimethylethyl)-4H-selenopyrylium] grouping, $R^3$ is a propyl group, and $R^1$, $R^2$ and $R^4$ are each a hydrogen atom, namely a 4-[[2-propylamino-3-[[2,6-bis[1,1-dimethylethyl]seleno-4H-pyran-4-ylidene]methyl]-4-oxo-2-cyclobuten-1-ylidene]methyl]-2,6-bis[1,1-dimethylethyl]selenopyrylium salt;

l. $Q^1$ is a 2-(1,1-dimethylethyl)-6-methoxybenz[b]-4H-thiopyran-4-ylidene grouping, $Q^2$ is a 4-[2-(1,1-dimethylethyl)-6-methoxybenz[b]-4H-thiopyrylium] grouping, $R^1$, $R^2$ and $R^4$ are each a hydrogen atom, and $R^3$ is a but-2-yl group, namely, a 4-[[3-[[2-[1,1-dimethylethyl]-6-methoxybenz[b]-4Hthiopyran-4-ylidene]methyl]-4-oxo-2-[propylamino]-2-cyclobuten-1-ylidene]methyl]-2-[1,1-dimethylethyl]-6-methoxybenz[b]thiopyrylium salt;

m. $Q^1$ is a 6-[but-2-oxy]-2-(1,1-dimethylethyl)benz[b]-4H-thiopyran-4-ylidene grouping, $Q^2$ is a 4-[2-(1,1-dimethylethyl)-6-[but-2-oxy]benz[b]-4H-thiopyrylium] grouping, $R^1$, $R^2$ and $R^4$ are each a hydrogen atom, and $R^3$ is a propyl group, namely, a 6-[but-2-oxy]-4-[[3-[[6-[but-2-oxy]-2-[1,1-dimethylethyl]benz[b]-4H-thiopyran-4-ylidene]-methyl]-4-oxo-2-[propylamino]-2-cyclobuten-1-ylidene]methyl]-2-[1,1-dimethylethyl]benz[b]thiopyrylium salt; and n. $Q^1$ is a 6-[but-2-oxy]-2-(1,1-dimethylethyl)benz[b]-4H-thiopyran-4-ylidene grouping, $Q^2$ is a 4-[6-[but-2-oxy]-2-(1,1-dimethylethyl)benz[b]-4H-pyrylium] grouping, $R^1$, $R^2$ and $R^4$ are each a hydrogen atom, and $R^3$ is a propyl group, namely, a 6-[but-2-oxy]-4-[[2-[propylamino]-3-[[6-[but-2-oxy]2-[1,1-dimethylethyl]-benz[b]-4H-thiopyran-4-ylidene]methyl]-4-oxo-2-cyclobuten-1-ylidene]methyl]-2-[1,1-dimethylethyl]benz[b]pyrylium salt.

Correspondingly, specific preferred squaric acid derivatives of Formula II are those in which:

a. $Q^1$ is a 2-(1,1-dimethylethyl)-7-diethylaminobenz[b]-4H-pyran-4-ylidene grouping, and $R^1$, $R^3$ and $R^4$ are each a hydrogen atom, namely 3-amino-4-[[7-diethylamino-2-[1,1-dimethylethyl]benz[b]-4H-pyran-4-ylidene]methyl]cyclobut-3-ene-1,2-dione;

b. $Q^1$ is a 2-(1,1-dimethylethyl)-7-diethylaminobenz[b]-4H-pyran-4-ylidene grouping, $R^1$ is a hydrogen atom, and $R^3$ and $R^4$ are each an ethyl group, namely 3-diethylamino-4-[[7-diethylamino-2-[1,1-dimethylethyl]benz[b]-4H-pyran-4-ylidene]methyl]cyclobut-3-ene-1,2-dione;

c. $Q^1$ is a 2-(1,1-dimethylethyl)-7-diethylaminobenz[b]-4H-pyran-4-ylidene grouping, $R^3$ is a butyl group and $R^1$ and $R^4$ are each a hydrogen atom, namely 3-butylamino-4-[[7-diethylamino-2-[1,1-dimethylethyl]benz[b]-4H-pyran-4-ylidene]methyl]cyclobut-3-ene-1,2-dione;

d. $Q^1$ is a 2-(1,1-dimethylethyl)-7-diethylaminobenz[b]-4H-pyran-4-ylidene grouping, $R^3$ is a —$CH_2CH_2SO_3H$ grouping, and $R^1$ and $R^4$ are each a hydrogen atom, namely 2-(3-sulfonatoprop-1-ylamino)-4-[[7-diethylamino-2-[1,1-dimethylethyl]benz[b]-4H-pyran-4-ylidene]methyl]cyclobut-3-ene-1,2-dione;

e. $Q^1$ is a 2,6-bis(1,1-dimethylethyl)-4H-thiopyran-4-ylidene grouping, and $R^1$, $R^3$ and $R^4$ are each a hydrogen atom, namely 3-amino-4-[[2,6-bis-[1,1-dimethylethyl]thio-4H-pyran-4-ylidene]methyl]cyclobut-3-ene-1,2-dione;

f. $Q^1$ is a 2,6-bis(1,1-dimethylethyl)-4H-thiopyran-4-ylidene grouping, $R^1$ is a methyl group, and $R^3$ and $R^4$ are each a hydrogen atom, namely 3-amino-4-[1-[2,6-bis[1,1-dimethylethyl]thio-4H-pyran-4-ylidene]eth-1-yl]cyclobut-3-ene-1,2-dione;

g. $Q^1$ is a 2,6-bis(1,1-dimethylethyl)-4H-thiopyran-4-ylidene grouping, $R^1$ is a methyl group, $R^3$ is a butyl group and $R^4$ is a hydrogen atom, namely 3-butylamino-4-[1-[2,6-bis[1,1-dimethylethyl]thio-4H-pyran-4-ylidene]-eth-1-yl]cyclobut-3-ene-1,2-dione;

h. $Q^1$ is a 2,6-bis(1,1-dimethylethyl)-4H-selenopyran-4-ylidene grouping, and $R^1$, $R^3$ and $R^4$ are each a hydrogen atom, namely 3-amino-4-[[2,6-bis-[1,1-dimethylethyl]seleno-4H-pyran-4-ylidene]methyl]cyclobut-3-ene-1,2-dione;

i. $Q^1$ is a 2,6-bis(1,1-dimethylethyl)-4H-selenopyran-4-ylidene grouping, $R^3$ is a propyl group, and $R^1$ and $R^4$ are each a hydrogen atom, namely 3-n-propylamino-4-[[2,6-bis[1,1-dimethylethyl]seleno-4H-pyran-4-ylidene]-methyl]-cyclobut-3-ene-1,2-dione;

j. $Q^1$ is a 2-(1,1-dimethylethyl)-6-[but-2-oxy]benz[b]-4H-thiopyran-4-ylidene grouping, $R^3$ is is a propyl group, and $R^1$ and $R^4$ are each a hydrogen atom, namely 4-[[2-[1,1-dimethylethyl]-6-[but-2-oxy]benz[b]-4H-thiopyran-4-ylidene]methyl]-3-propylaminocyclobut-3-ene-1,2-dione; and k. $Q^1$ is a 2-(1,1-dimethylethyl)-6-[but-2-oxy]benz[b]-4H-pyran-4-ylidene grouping, $R^3$ is is a propyl group, and $R^1$ and $R^4$ are each a hydrogen atom, namely 4-[[2-[1,1-dimethylethyl]-6-[but-2-oxy]benz[b]-4H-pyran-4-ylidene]methyl]-3-propylaminocyclobut-3-ene-1,2-dione.

The dyes produced by the processes of the present invention may be used in any of the applications in which prior art near infra-red absorbers have been used. Thus, the dyes may be used as dyes in printing inks intended to provide markings which can be read under near infra-red radiation, for example, on packages of container items intended to be scanned by near infra-red laser scanners. At least some of the present dyes may also be useful as charge transfer materials for use in xerography, electrophotography and similar processes, and as laser dyes.

However, because of their high extinction coefficients in the near infra-red region, the dyes produced by the present processes are especially useful in processes for generating heat in a medium; in such a process at least part of the medium is exposed to near infra-red actinic radiation of a frequency absorbed by the dye, so that the radiation is absorbed by the dye and heat is generated within the parts of the medium exposed to the radiation. Typically, in such a process, the radiation is provided by a laser. The medium may also comprise a thermally sensitive material capable of undergoing a color change upon exposure to heat; the medium is exposed imagewise to the radiation, and the heat generated by the dye is sufficient to effect a color change in the thermally sensitive material, so that an image is formed in the medium. Thus, for example, the present dyes may be used as the near infra-red absorbers in the thermal imaging processes described in U.S. Pat. Nos. 4,602,263 and 4,826,976, and in the aforementioned copending applications U.S. Ser. Nos. 07/695,641; 07/696,196 and 07/695,932. These imaging processes rely upon the irreversible unimolecular fragmentation of one or more thermally unstable carbamate moieties of an organic compound to effect a visually discernible color shift from colorless to colored, from colored to colorless or from one color to another.

In such a process, preferably the thermally sensitive material is originally substantially colorless and is converted by the heat generated to a colored material in exposed areas of the image. Multi-colored images may be produced using a heat-sensitive element containing an imaging layer of colorless imaging compound (leuco dye) for forming a yellow image, an imaging layer of colorless imaging compound for forming a cyan image, and an imaging layer of colorless imaging compound for forming a magenta image. Preferred leuco dyes, and processes for their preparation, are described in U.S. Pat. No. 4,663,518, and other preferred yellow-forming leuco dyes are described in application U.S. Ser. No. 07/548,223, filed Jun. 29, 1990.

In the production of such multi-color images, each imaging layer contains, in addition to the leuco dye, an infra-red absorber selected such that the three infra-red absorbers absorb radiation at different predetermined wavelengths above 700 nm sufficiently separated so that each imaging layer may be exposed separately and independently of the others by using infra-red radiation at the particular wavelengths selectively absorbed by the respective infra-red absorbers. As an illustration, the yellow, magenta and cyan precursors may have infra-red absorbers associated therewith that absorb radiation at (say) 760 nm, 820 nm and 880 nm, respectively, and may be addressed by laser sources, for example, infra-red laser diodes emitting radiation at these respective wavelengths so that the three imaging layers can be exposed independently of one another. While each layer may be exposed in a separate scan, it is usually preferred to expose all of the imaging layers simultaneously in a single scan using multiple laser sources of the appropriate wavelengths. Instead of using superimposed imaging layers, the heat-sensitive compounds and associated infra-red absorbers may be arranged in an array of side-by-side dots or stripes in a single recording layer.

The dyes of the present invention may also be used in the acid-generating imaging process described in copending application Ser. No. 07/965,161 of Stephen J. Telfer, filed Oct. 23, 1992 (now U.S. Pat. No. 5,286,612).

A preferred thermal imaging medium of this invention will now be described, though by way of illustration only, with reference to FIG. 6 of the accompanying drawings, which is a schematic cross-section through the imaging medium. The thicknesses of the various layers shown in the drawing are not to scale.

Figure 6:
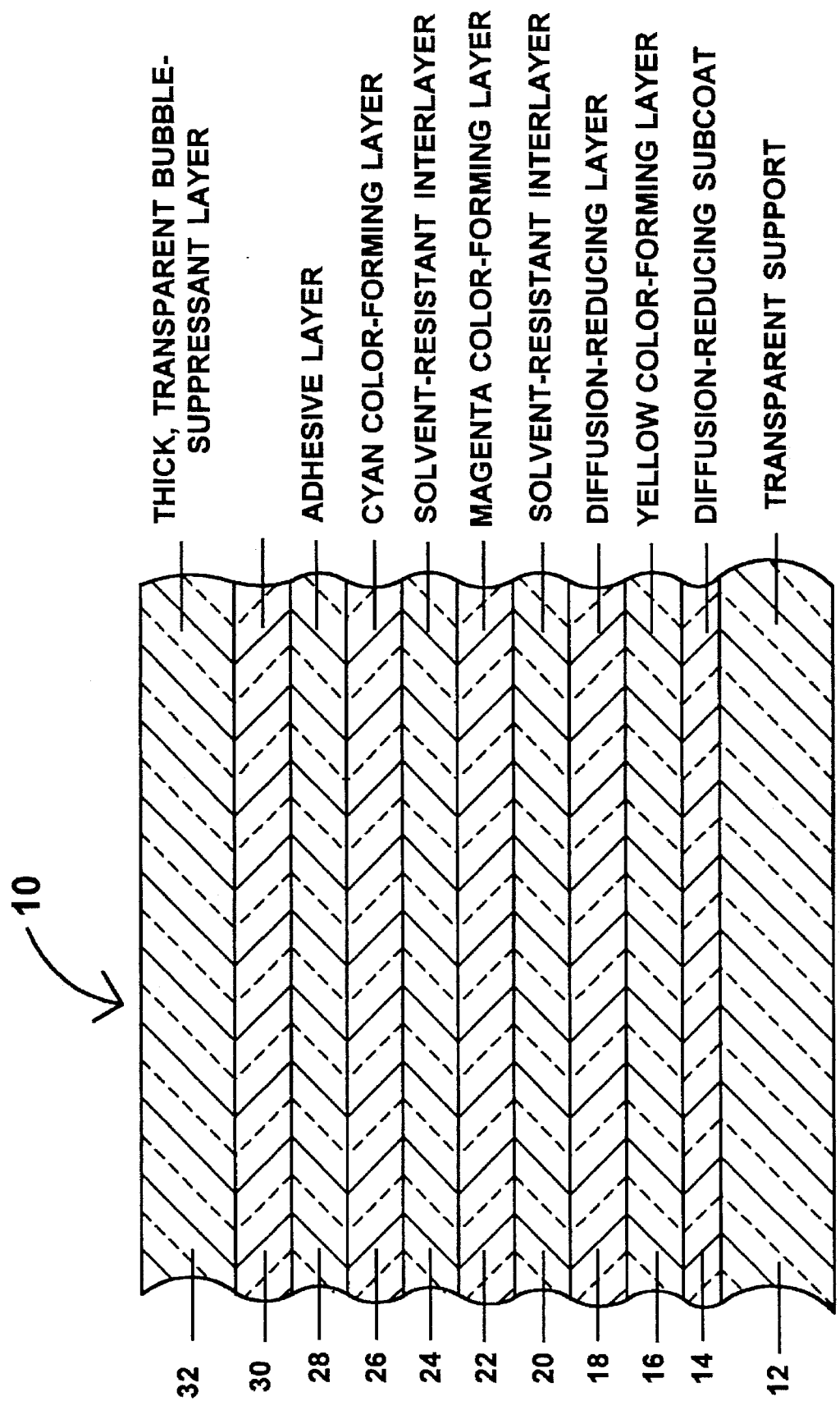
FIG. 6 shows a schematic cross-section through a preferred imaging medium of the present invention incorporating infra-red dyes of the present invention.

The imaging medium (generally designated 10) shown in FIG. 6 is intended for use in the production of transparencies and comprises a substantially transparent support 12 formed of 4 mil (101 μm) poly(ethylene terephthalate) (PET) film incorporating an ultra-violet absorber. Appropriate PET films are readily available commercially, for example as P4C1A film from DuPont de Nemours., Wilmington, Del.

The imaging medium 10 also comprises a diffusion-reducing subcoat 14 approximately 1 μm thick formed from a 10:1 w/w mixture of a water-dispersible styrene acrylic polymer (Joncryl 538 sold by S.C. Johnson & Son, Inc., Racine, Wis. 53403) and a water-soluble acrylic polymer (Carboset 526 sold by The B.F. Goodrich Co., Akron, Ohio 44313). The presence of the minor proportion of water-soluble acrylic polymer reduces the tendency for the layer 14 to crack during the coating process. The diffusion-reducing subcoat 14, which has a glass transition temperature of approximately 55° C., serves the function of a conventional subcoat, namely increasing the adhesion of the imaging layer 16 (described in detail below) to the support 12. The subcoat 14 also serves to reduce or eliminate migration of dye compound from the imaging layer 16 after imaging; if a conventional subcoat were employed in place of the diffusion-reducing subcoat 14, diffusion of the dye compound from the layer 16 into the subcoat after imaging might cause loss of sharpness of the image. The subcoat 14 is coated onto the support 12 from an aqueous medium containing the water-dispersible and water-soluble polymers.

A yellow imaging layer 16 is in contact with the diffusion-reducing subcoat 14. This imaging layer 16 is approximately 5 μm thick and comprises approximately 47.5 parts by weight of a leuco dye of the formula:

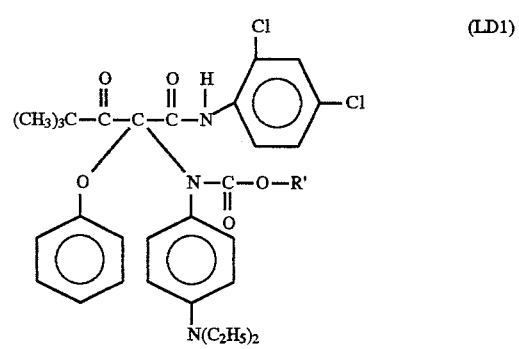

(LD1)

in which R' is a tertiary butyl group (the compounds in which R' is an isobutyl or benzyl group may alternatively be used), 1.6 parts by weight of an infra-red dye of the formula:

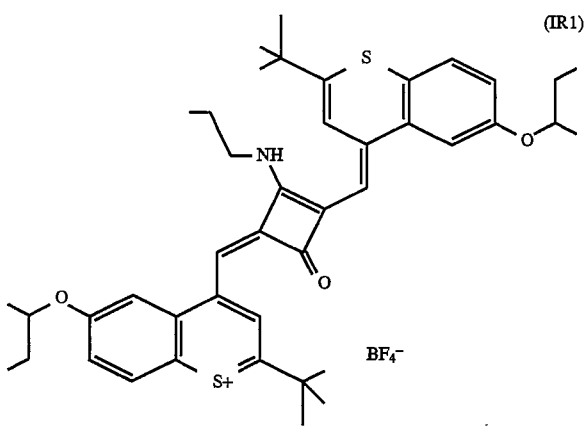

(which may be produced in a manner exactly analogous to the reaction of Example 33 substituting the 6-[2-butoxy] salt for the 6-methoxy salt used in that Example), 3.3 parts by weight of a hindered amine stabilizer (HALS-63, sold by Fairmount Chemical Co.), and 47.5 parts by weight of a poly(methyl methacrylate) binder (Elvacite 2021, sold by DuPont de Nemours, Wilmington, Del.; this material is stated by the manufacturer to be a methyl methacrylate/ethyl acrylate copolymer, but its glass transition temperature approximates that of poly(methyl methacrylate)). This binder has a glass transition temperature of approximately 110° C. The imaging layer 16 is applied by coating from a mixture of heptanes and methyl ethyl ketone.

(Alternatively, the infra-red dye of Formula IR1 above may be replaced by an infra-red dye of the formula:

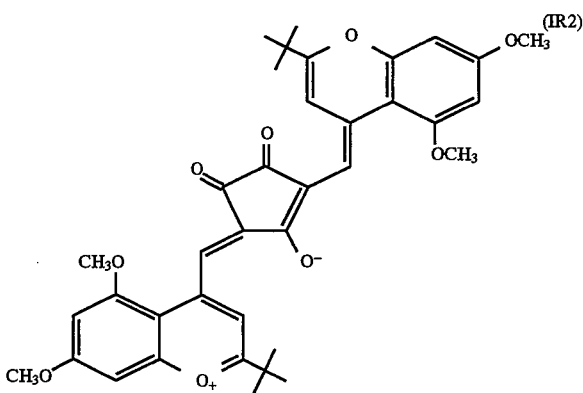

which may be prepared as described in the aforementioned U.S. Pat. No. 5,405,976; essentially, this dye is produced by condensing two moles of a 2-(1,1-dimethylethyl)-5,7-dimethoxy-4-methylbenzpyrylium salt with a croconate salt.

Superposed on the yellow imaging layer 16 is a diffusion-reducing layer 18, which, like the first diffusion-reducing layer 14, serves to prevent migration of dye compound from the yellow imaging layer 16 on storage after imaging. The diffusion-reducing layer 18, which is approximately 2 μm thick, is formed of a water-dispersible styrene acrylic polymer (Joncryl 138 sold by S.C. Johnson & Son, Inc., Racine, Wis. 53403), and is coated from an aqueous dispersion. This layer has a glass transition temperature of approximately 60° C.

The next layer of the imaging medium 10 is a solvent-resistant interlayer 20 approximately 4.6 μm thick and composed of a major proportion of partially cross-linked polyurethane (NeoRez XR-9637 polyurethane sold by ICI Resins US, Wilmington, Mass.) and a minor proportion of poly(vinyl alcohol) (Airvol 540, sold by Air Products and Chemicals, Inc., Allentown, Pa. 18195). This solvent-resistant interlayer 20 is coated from an aqueous dispersion. The interlayer 20 not only helps to thermally insulate the imaging layers 14 and 22 (described below) from one another during imaging, but also prevents disruption and/or damage to the yellow imaging layer 16 and the diffusion-reducing layer 18 during coating of the magenta imaging layer 22. Since the yellow imaging layer 16 and the magenta imaging layer 22 are both coated from organic solution, if a solvent-resistant interlayer were not provided on the layer 16 before the layer 22 was coated, the organic solvent used to coat the layer 22 might disrupt, damage or extract leuco dye or infra-red absorber from the layer 16. Provision of the solvent-resistant interlayer 20, which is not dissolved by and does not swell in the organic solvent used to coat the layer 22, serves to prevent disruption of or damage to the layer 16 as the layer 22 is coated. Furthermore, the solvent-resistant interlayer 20 serves to prevent the magenta leuco dye, infra-red dye and hindered amine light stabilizer from the layer 22 sinking into the diffusion-reducing layer 18 and the yellow imaging layer 16 as the layer 22 is being coated.

Superposed on the solvent-resistant interlayer 20 is the magenta imaging layer 22, which is approximately 3 μm thick and comprises approximately 47.25 parts by weight of a leuco dye of the formula:

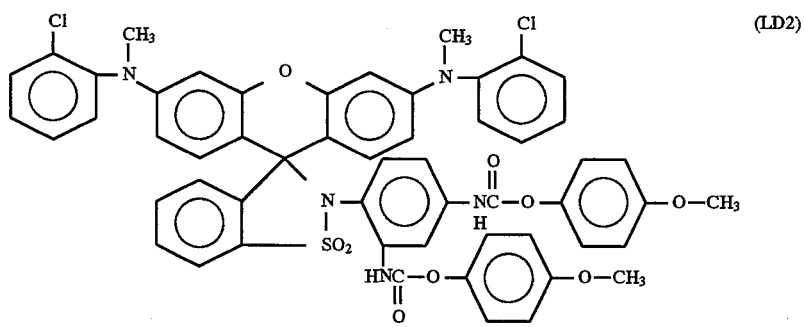

(this leuco dye may be prepared by the methods described in U.S. Pat. Nos. 4,720,449 and 4,960,901), approximately 3.4 parts by weight of zinc acetate (thus giving a leuco dye: zinc cation molar ratio of about 1:0.4), 1.62 parts by weight of an infra-red dye of the formula:

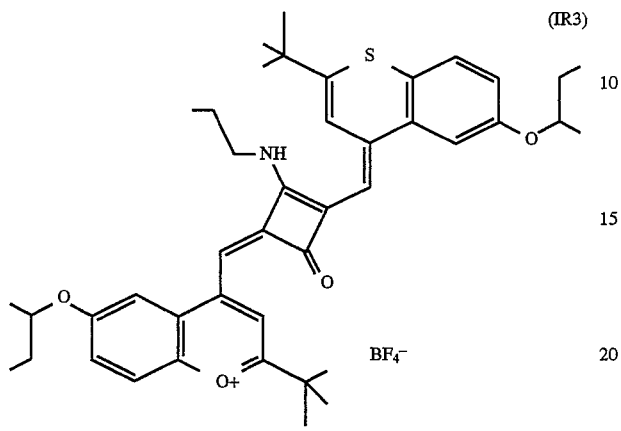

(which may be produced in a manner exactly analogous to the reaction of Example 27 substituting the 6-[2-butoxy] salt for the 6-methoxy salt used in that Example), 3.6 parts by weight of a hindered amine stabilizer (HALS-63), 0.27 parts by weight of a wetting agent, and 47.25 parts by weight of a polyurethane binder (Estane 5715, supplied by The B.F. Goodrich Co., Akron, Ohio 44313). The imaging layer 22 is applied by coating from a cyclohexanone/methyl ethyl ketone mixture.

Alternatively, the infra-red dye of Formula IR3 above may be replaced by the dye of formula:

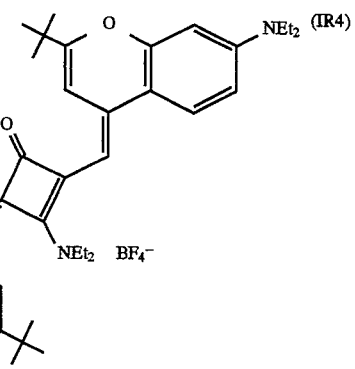

(prepared in Example 22 below), or by the dye of formula:

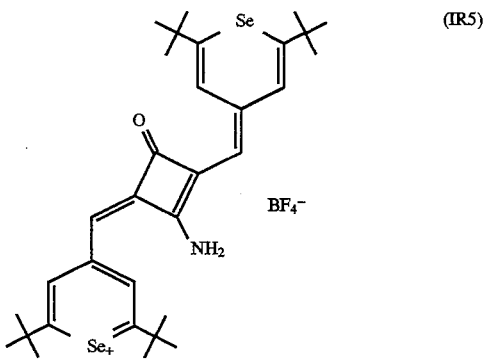

(prepared in Example 19 below).

On the imaging layer 22 is coated a second solvent-resistant interlayer 24 which is formed from the same material, and coated in the same manner as, the solvent-resistant interlayer 20.

Superposed on the second solvent-resistant interlayer 24 is a cyan imaging layer 26, which is approximately 3 μm thick and comprises approximately 49.5 parts by weight of a leuco dye of the formula:

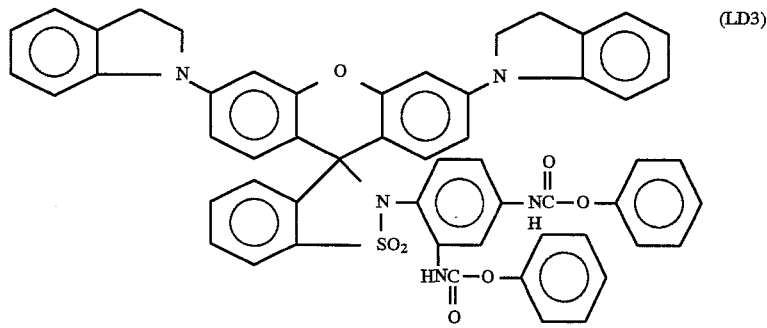

(this leuco dye may be prepared by the methods described in the aforementioned U.S. Pat. Nos. 4,720,449 and 4,960,901), approximately 3.97 grams of zinc acetate (thus giving a leuco dye: zinc cation molar ratio of about 1:0.4), 1.62 parts by weight of an infra-red dye of the formula:

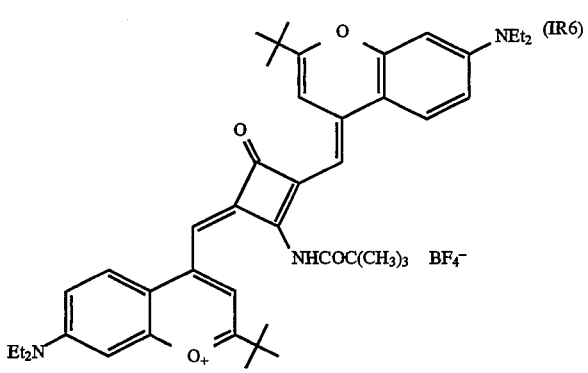

(prepared in Example 25 below), 0.2 parts of a wetting agent, and 49.5 parts by weight of a polyurethane binder (Estane 5715). The imaging layer 26 is applied by coating from methyl ethyl ketone.

(Alternatively, the infra-red dye of Formula IR6 above may be replaced by the dye of formula:

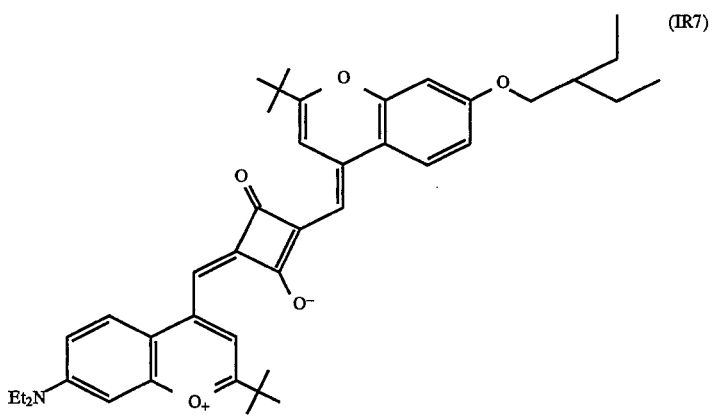

which is preferably prepared by the process described in the aforementioned copending application U.S. Ser. No. 07/696,222; essentially this process comprises reacting a diester, diacid chloride or monoester monoacid chloride of squaric acid with a 2-(1,1-dimethylethyl)-7-diethylamino-4-methylbenzpyrylium salt and hydrolysing to produce a compound of the formula:

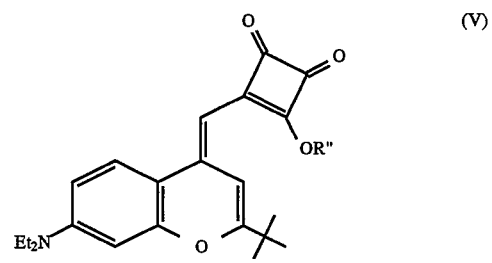

and then reacting this compound with a 7-alkoxy-2-(1,1-dimethylethyl)-4-methylbenzpyrylium salt to give the final infra-red dye of Formula IR7.

As already indicated, the layers 14–26 of the imaging medium 10 are produced by coating on to the transparent rapport 12. However, the remaining layers of the imaging medium 10, namely the transparent bubble-suppressant layer 32, the ultraviolet filter layer 30 and the adhesive layer 28 are not coated on to the layer 26 but rather are prepared as a separate unit and then laminated to the remaining layers of the medium.

The transparent bubble-suppressant layer 32 is a 1.75 mil (44 μm) PET film, a preferred film being that sold as ICI 505 film by ICI Americas, Inc., Wilmington, Del. The bubble-suppressant layer 32 prevents the formation of bubbles in the imaging layers 16, 22 and 26 of the imaging medium 10 during imaging.

The ultraviolet filter layer 30 serves to protect the imaging layers 16, 22 and 26 from the effects of ambient ultraviolet radiation. It has been found that the leuco dyes are susceptible to undergoing color changes when exposed to ultraviolet radiation during storage before or after imaging; such color changes are obviously undesirable since they increase the $D_{min}$ of the image and may distort the colors therein. The ultraviolet filter layer 30 is approximately 5 μm thick and comprises approximately 83 percent by weight of a poly (methyl methacrylate) (Elvacite 2043, sold by DuPont de Nemours, Wilmington, Mass.), 16.6 percent by weight of an ultraviolet filter (Tinuvin 328 sold by Ciba-Geigy, Ardsdale, N.Y.) and 0.4 percent by weight of a wetting agent. The ultraviolet filter layer 30 is prepared by coating on to the bubble-suppressant layer 32 from a solution in methyl ethyl ketone.

The adhesive layer, which is approximately 2 μm thick, is formed of a water-dispersible styrene acrylic polymer (Joncryl 138 sold by S.C. Johnson & Son, Inc., Racine, Wis. 53403) and is coated on to the ultraviolet filter layer 30 from an aqueous dispersion.

After the layers 30 and 28 have been coated on to the bubble-suppressant layer 32, the entire structure containing these three layers is laminated under heat (approximately 225° F., 107° C.) and pressure to the structure containing the layers 12–26 to form the complete imaging medium 10.

If desired, the bubble-suppressant layer 32 may be formed by coating, rather than by lamination of a pre-formed film on to the layers 12–26. If the bubble-suppressant layer 32 is to be formed by coating, it is convenient to incorporate an ultra-violet absorber into the bubble-suppressant layer, thereby avoiding the need for a separate ultra-violet absorber layer. Thus, in this case, the layer 28 is coated on to the layer 26 using the solvent already described, and then the bubble-suppressant layer 32 containing the ultra-violet absorber may be coated on to the layer 28 from an aqueous medium.

The medium 10 is imaged by exposing it simultaneously to the beams from three infra-red lasers having wavelengths of approximately 790, 850 and 920 nm. The 920 nm beam images the yellow imaging layer 16, the 850 nm beam images the magenta imaging layer 22 and the 790 nm beam images the cyan imaging layer 26. Thus, a multicolor image is formed in the imaging medium 10, and this multicolor image requires no further development steps. Furthermore, the medium 10 may be handled in normal room lighting prior to exposure, and the apparatus in which the imaging is performed need not be light-tight.

Alternatively, the present dyes may be used in a thermal imaging process in which the medium comprises one layer of a multi-layer structure, this structure further comprising a support layer disposed on one side of the medium and a colored layer adhering to the opposed side of the medium. In this type of thermal imaging process, the heat generated on exposure of the dye to actinic radiation causes increased adhesion of the colored layer to the support layer, such that upon application of a peeling force to the colored-layer, the colored layer will peel from the support layer in areas which have not been exposed to the radiation, but in areas which have been exposed to radiation the colored layer will remain attached to the support layer. A preferred thermal imaging process of this type is described and claimed in International Patent Application No. PCT/US87/03249 (Publication No. WO88/04237).

From the foregoing description, it will be seen that the present invention provides near infra-red dyes with enhanced compatibility with a variety of media and which can be arranged to have absorptions within narrow wavelength ranges. Furthermore, these dyes can contain a variety of functional groups. The processes of the present invention enable asymmetric infra-red dyes of the invention to be synthesized without the need to separate mixtures of asymmetric and symmetric dyes.

The following Examples are now given, though by way of illustration only, to show details of particularly preferred reagents, conditions and techniques used in the processes of the present invention.

EXAMPLES 1–15

First Process of the Invention

The following Examples 1–15 illustrate the first process of the invention, that is to say reactions analogous to reaction K→L, shown in FIG. 2, together with certain reactions used for the preparation of the necessary starting materials, and conversion of compounds of Formula II to other compounds of Formula II.

Example 1

Preparation of 4-[[7-diethylamino-2-(1,1-dimethylethyl)benz[b]-4H-pyran-4-ylidene]methyl]-3-butoxycyclobut-3-ene-1,2-dione This Example illustrates the preparation, by a reaction analogous to B+H→K shown in FIG. 1, of the squaric acid derivative K in which $R^1$ is a hydrogen atom.

A solution of 7-diethylamino-2-(1,1-dimethylethyl)-4-methylbenzpyrylium tetrafluoroborate (3.57 g, 10 mmol, prepared as described in the aforementioned copending application U.S. Ser. No. 07/616,639) in dichloromethane (20 mL) was added dropwise over two hours to a solution of dibutyl squarate (2.5 g, 11 mmol, available from Aldrich Chemical Company, Milwaukee, Wis.) and triethylamine (2.02 g, 20 mmol) in dichloromethane (30 mL) at room temperature. After the addition had been completed, the reaction mixture was heated under reflux for three hours. The solvent was then removed and diethyl ether (50 mL) was added. The ether solution was filtered and the solid residue was washed with more ether (50 mL). The combined ether extracts were concentrated, and the crude product thus obtained was purified by flash chromatography on silica gel with 30% ether/hexanes as eluent to give 4-[[7-diethylamino-2-(1,1-dimethylethyl)benz[b]-4H-pyran4-ylidene]methyl]-3-butoxycyclobut-3-ene-1,2-dione as a red solid (1.35 g, 29% yield) which melted at 145°–146° C. The structure of this compound was confirmed by mass spectroscopy and by $^1$H and $^{13}$C NMR spectroscopy.

(The filtrate from the ether extraction was collected, dissolved in dichloromethane, washed sequentially with 1M hydrochloric acid, a saturated solution of sodium hydrogen carbonate and brine, and dried over magnesium sulfate. Removal of solvent yielded 3,4-bis[[7-diethylamino-2-(1,1-dimethylethyl)benz[b]-4H-pyran-4-ylidene]methyl] cyclobut-3-ene-1,2-dione as a green solid (1.14 g, 37% yield) which did not melt below 300° C. The structure of this compound was confirmed by mass spectroscopy and by $^1$H and $^{13}$C NMR spectroscopy.)

Examples 2–4

Preparation of squaric acid derivatives, analogues of the compound prepared in Example 1

The following squaric acid derivatives, which differ from the derivative prepared in Example 1 in the group $R^1$ and/or by replacement of the benzpyrylium grouping with a thiopyrylium or selenopyrylium grouping, were prepared in the same manner as in Example 1.

Example 2

4-[[2,6-bis[1,1-dimethylethyl]thiopyran-4-ylidene] methyl]-3-butoxy-cyclobut-3-ene-1,2-dione This is the compound of Formula III in which $Q^1$ is a 2,6-bis(1,1-dimethylethyl)-4H-thiopyran-4-ylidene grouping, $R^1$ is a hydrogen atom, and A is a butoxy group. The starting material used was 2,6-bis[1,1-dimethylethyl]-4-methylthiopyrylium tetrafluoroborate, the preparation of which is described in U.S. Pat. No. 4,343,948 to Kawamura.

Example 3

4-[1-[2,6-bis[1,1-dimethylethyl]thiopyran-4-ylidene] eth-1-yl]-3-butoxycyclobut-3-ene-1,2-dione This is the compound of Formula III in which $Q^1$ is a 2,6-bis(1,1-dimethylethyl)-4H-thiopyran-4-ylidene grouping, $R^1$ is a methyl group and A is a butoxy group. The starting material used was 2,6-bis[1,1-dimethylethyl]-4-ethylthiopyrylium tetrafluoroborate.

Example 4

4-[[2,6-bis[1,1-dimethylethyl]selenopyran-4-ylidene] methyl]-3-butoxy-cyclobut-3-ene-1,2-dione This is the compound of Formula III in which $Q^1$ is a 2,6-bis(1,1-dimethylethyl)-4H-selenopyran-4-ylidene grouping, $R^1$ is a hydrogen atom, and A is a butoxy group. The starting material used was 2,6-bis[1,1-dimethylethyl]-4-methylselenopyrylium tetrafluoroborate, the preparation of which is described in the aforementioned copending application U.S. Ser. No. 07/696,222.

Example 5

Preparation of 3-amino-4-[[7-diethylamino-2-[1,1-dimethylethyl]-benz[b]-4H-pyran-4-ylidene]methyl] cyclobut-3-ene,1,2-dione This Example illustrates the preparation, by the reaction K→L shown in FIG. 2, of the aminosquaric acid derivative L in which $R^1$, $R^3$ and $R^4$ are each a hydrogen atom, this derivative being the derivative of Formula II in which $Q^1$ is a 2-(1,1-dimethylethyl)-7-diethylaminobenz[b]-4H-pyran-4-ylidene grouping, and $R^1$, $R^3$ and $R^4$ are each a hydrogen atom.

A 30% solution of ammonium hydroxide (2 mL) was added to a solution of 4-[[7-diethylamino-2-[1,1-dimethylethyl]benz[b]-4H-pyran-4-ylidene]methyl]-3-butoxycyclobut-3-ene-1,2-dione (300 mg, 0.71 mmol, prepared in Example 1 above) in tetrahydrofuran (THF, 10 mL) and the resultant mixture was stirred at room temperature for 3 hours. Dichloromethane and water were then added and the layers were separated. Drying of the organic layer with magnesium sulfate followed by removal of the solvent afforded the desired product in essentially quantitative yield as a red solid which melted at 261°–264° C. The product was of sufficient purity to be used directly in the next step. The $^{13}C$ NMR spectrum of the product was: $\delta_C$ (75 MHz in $d_6$-DMSO) 189.1, 188.0, 180.1, 179.9, 166.7, 163.6, 154.3, 149.9, 137.6, 124.8, 110.1, 108.8, 102.2, 97.1, 96.1, 43.7, 35.6, 27.8 and 12.4 ppm. The structure of this compound was also confirmed by mass spectroscopy and by $^1H$ NMR spectroscopy of a sample prepared in an analogous, small-scale reaction.

Examples 6–8

Preparation of Aminosquaric Acid Derivatives

The following aminosquaric acid derivatives were prepared from the squaric acid derivatives of Examples 2–4 respectively above using the same reaction conditions as in Example 5 above.

Example 6

3-amino-4-[[2,6-bis[1,1-dimethylethyl]thio-4H-pyran-4-ylidene]methyl]cyclobut-3-ene-1,2-dione This is the compound of Formula II in which $Q^1$ is a 2,6-bis(1,1-dimethylethyl)-4H-thiopyran-4-ylidene grouping, and $R^1$, $R^3$ and $R^4$ are each a hydrogen atom. The structure of this compound was confirmed by mass spectroscopy and by $^1H$ and $^{13}C$ NMR spectroscopy; the $^{13}C$ spectrum was: $\delta_C$ (75 MHz in CDCl$_3$) 188.7, 188.3, 177.5, 168.1, 156.8, 156.4, 145.6, 121.4, 120.9, 104.7, 38.9, 38.0, 30.5 and 30.3 ppm.

Example 7

3-amino-4-[1-[2,6-bis[1,1-dimethylethyl]thio-4H-pyran-4-ylidene]eth-1-yl]cyclobut-3-ene-1,2-dione This is the compound of Formula II in which $Q^1$ is a 2,6-bis(1,1-dimethylethyl)-4H-thiopyran-4-ylidene grouping, $R^1$ is a methyl group, and $R^3$ and $R^4$ are each a hydrogen atom. The structure of this compound was confirmed by mass spectroscopy and by $^1H$ and $^{13}C$ NMR spectroscopy; the $^{13}C$ spectrum was: $\delta_C$ (75 MHz in $d_6$-DMSO) 192.1, 190.0, 180.4, 169.5, 151.3, 146.9, 134.5, 120.0, 115.8, 112.2, 37.7, 37.5, 29.9, 29.8 and 14.9 ppm.

Example 8

3-amino-4-[[2,6-bis-[1,1-dimethylethyl]seleno-4H-pyran-4-ylidene]methyl]cyclobut-3-ene-1,2-dione This is the compound of Formula II in which $Q^1$ is a 2,6-bis(1,1-dimethylethyl)-4H-selenopyran-4-ylidene grouping, and $R^1$, $R^3$ and $R^4$ are each a hydrogen atom. The structure of this compound was confirmed by mass spectroscopy and by $^1H$ and $^{13}C$ NMR, spectroscopy; the $^{13}C$ spectrum was: $\delta_C$ (75 MHz in CDCl$_3$) 189.0, 188.7, 178.0, 167.8, 159.7, 158.6, 146.1, 122.6, 121.8, 108.4, 40.0, 39.1, 31.0 and 30.8 ppm.

Example 9

Preparation of 3-diethylamino-4-[[7-diethylamino-2-[1,1-dimethylethyl]benz[b]-4H-pyran-4-ylidene] methyl]cyclobut-3-ene-1,2-dione This Example illustrates the preparation, by the reaction K○L shown in FIG. 2, of the aminosquaric acid derivative L in which $R^1$ is a hydrogen atom, and $R^3$ and $R^4$ are each an ethyl group, this derivative being the derivative of Formula II in which $Q^1$ is a 2-(1,1-dimethylethyl)-7-diethylaminobenz[b]-4H-pyran-4-ylidene grouping, $R^1$ is a hydrogen atom, and $R^3$ and $R^4$ are each an ethyl group.

Diethylamine (20 mg, 0.27 mmol) was added to a solution of 4-[[7-diethylamino-2-(1,1-dimethylethyl)benz[b]-4H-pyran-4-ylidene]methyl]-3-butoxycyclobut-3-ene-1,2-dione (80 mg, 0.19 mmol, prepared as in Example 1 above) in dichloromethane (1 mL) and the resultant mixture was stirred at room temperature for 6 hours. Removal of the solvent under reduced pressure afforded the desired aminosquaric acid derivative, which was washed with ether to give a red solid (76 mg, 95% yield) which melted at 148°–150° C. The structure of this compound was confirmed by mass spectroscopy and by $^1H$ and $^{13}C$ NMR spectroscopy; the $^{13}C$ spectrum was:

$\delta_C$ (75 MHz in CDCl$_3$) 188.8, 187.9, 175.8, 166.0, 164.6, 155.0, 149.8, 139.0, 124.1, 109.7, 109.5, 102.8, 97.8, 95.2, 44.5, 36.1, 28.0, 14.9 and 12.6 ppm.

Examples 10–12

Preparation of Aminosquaric Acid Derivatives

The following aminosquaric acid derivatives were prepared using the same reaction conditions as in Example 9 above.

Example 10

3-butylamino-4-[[7-diethylamino-2-[1,1-dimethylethyl]benz[b]-4H-pyran-4-ylidene]methyl] cyclobut-3-ene-1,2-dione This is the aminosquaric acid derivative L in which $R^3$ is an n-butyl group and $R^1$ and $R^4$ are each a hydrogen atom, this derivative being the derivative of Formula II in which $Q^1$ is a 2-(1,1-dimethylethyl)-7-diethylaminobenz[b]-4H-pyran-4-ylidene grouping, $R^3$ is a butyl group and $R^1$ and $R^4$ are each a hydrogen atom. It is only necessary to substitute an equimolar amount of butylamine for the diethylamine used in Example 9. The structure of this compound was confirmed by mass spectroscopy and by $^1H$ and $^{13}C$ NMR spectroscopy; the $^{13}C$ spectrum was: $\delta_C$ (75 MHz in $d_6$-DMSO) 188.5, 187.1, 177.7, 165.5, 163.6, 154.3, 149.9, 137.7, 124.8, 110.1, 108.4, 102.2, 97.1, 96.1, 54.9, 43.7, 43.5, 35.6, 32.6, 27.7, 19.1, 13.5 and 12.4 ppm.

Example 11

3-butylamino-4-[1-[2,6-bis[1,1-dimethylethyl]thio-4H-pyran-4-ylidene]eth-1-yl]cyclobut-3-ene-1,2-dione This is the aminosquaric acid derivative of Formula II in which $Q^1$ is a 2,6-bis(1,1-dimethylethyl)-4H-thiopyran-4- ylidene grouping, $R^1$ is a methyl group, $R^3$ is a butyl group and $R^4$ is a hydrogen atom, and is obtained by replacing the starting material of Example 10 with the squaric acid derivative prepared in Example 3 above. The structure of this compound was confirmed by mass spectroscopy and by $^1H$ and $^{13}C$ NMR spectroscopy; the $^{13}C$ spectrum was:

$\delta_C$ (75 MHz in CDCl$_3$) 190.1, 189.8, 178.6, 170.0, 153.0, 150.9, 135.7, 119.3, 116.0, 111.9, 45.1, 38.1, 33.3, 30.3, 19.6, 14.9 and 13.7 ppm.

Example 12

3-propylamino-4-[[2,6-bis[1,1-dimethylethyl]seleno-4H-pyran-4-ylidene]-methyl]cyclobut-3-ene-1,2-dione This is the aminosquaric acid derivative of Formula II in which $Q^1$ is a 2,6-bis(1,1-dimethylethyl)-4H-selenopyran-4-ylidene grouping, $R^3$ is a propyl group, and $R^1$ and $R^4$ are each a hydrogen atom. The starting materials used are propylamine and the squaric acid derivative prepared in Example 4 above. The structure of this compound was confirmed by mass spectroscopy and by $^1H$ NMR spectroscopy.

Example 13

Preparation of 2-(3-sulfonatoeth-1-ylamino)-4-[[7-diethylamino-2-[1,1-dimethylethyl]benz[b]-4H-pyran-4-ylidene]methyl]cyclobut-3-ene-1,2-dione This is the aminosquaric acid derivative L in which $R^3$ is (notionally) a —CH$_2$CH$_2$SO$_3$H grouping and $R^1$ and $R^4$ are each a hydrogen atom, this derivative being the derivative of Formula II in which $Q^1$ is a 2-(1,1-dimethylethyl)-7-diethylaminobenz[b]-4H-pyran-4-ylidene grouping, $R^3$ is (notionally) a —CH$_2$CH$_2$SO$_3$H grouping, and $R^1$ and $R^4$ are each a hydrogen atom.

4-[[7-Diethylamino-2-(1,1-dimethylethyl)benz[b]-4H-pyran-4-ylidene]methyl]-3-butoxycyclobut-3-ene-1,2-dione (155 mg, 0.36 mmol, prepared in Example 1 above), taurine (45 mg, 0.36 mmol) and triethylamine (40 mg, 0.4 mmol) were stirred overnight at room temperature in water/diglyme (5 mL/10 mL). The mixture was then concentrated under reduced pressure, removing the water and some of the diglyme. Ether was added, and a solid residue was formed, which was separated and washed with more ether. The remaining material was then treated with dichloromethane, which dissolved the desired product but not excess taurine, which was removed by filtration. Removal of dichloromethane gave orange crystals (80 mg) which were used in Example 25 below without further purification. The structure of this compound was continued by mass spectroscopy and by $^1H$ and $^{13}C$ NMR spectroscopy.

Example 14

Preparation of 4-[[2-[1,1-dimethylethyl]-6-methoxybenz[b]-4H-thiopyran-4-ylidene]methyl]-3-propylaminocyclobut-3-ene-1,2-dione This Example illustrates the preparation, by reactions analogous to B+F∘J shown in FIG. 1 and J∘L (i.e., a reaction analogous to K∘L shown in FIG. 2, but starting with the monoacid chloride rather than the monoester), of the aminosquaric acid derivative of Formula II in which $Q^1$ is a 2-[1,1-dimethylethyl]-6-methoxybenz[b]-4H-thiopyran-4-ylidene grouping, $R^3$ is an propyl group, and $R^2$ and $R^4$ are each a hydrogen atom.

A solution of 2-[1,1-dimethylethyl]-6-methoxy-4-methylbenzthiopyrylium tetrafluoroborate (31.0 g, 93 mmol, prepared in Example 32 below) in dry dimethylformamide (DMF, 200 mL) was added dropwise at room temperature under nitrogen to a solution of 3,4-dichlorocyclobut-3-ene-1,2-dione (15.7 g, 104 mmol, prepared as described in Schmidt, A. H, Synthesis, 1980, 963) in dry DMF (200 mL) over a period of 5 hours. A red-brown color developed. The reaction mixture was then cooled with an ice/water bath, and propylamine (71.9 g, 1.22 mol) was added in a slow stream over 10 minutes (a mildly exothermic reaction occurred). The dark red mixture was then stirred at room temperature for 17 hours, after which it was poured into a rapidly stirred mixture of ice/brine (1.5 L) and concentrated hydrochloric acid (100 mL). The solid which separated was collected by filtration, washed with water and air-dried to give the crude product as a red-brown powder. Purification was effected by dissolving this material in dichloromethane (1 L) and slurrying with silica gel (500 g of Selecto 142824 40 micron) for 10 minutes. The mixture was filtered, and the solid residue was washed with dichloromethane (10 100 mL aliquots). The solid residue was then set aside. The blue filtrate was treated in a similar manner with a further 250 g of the silica gel, and the cycle of filtration and washing was repeated. The solid residue was combined with that set aside earlier, and the desired product was extracted from the silica gel by slurrying with methanol for 10 minutes, followed by filtration. The filtrate was reserved, and the silica gel was washed with more methanol (10 100 mL aliquots). The combined methanol extracts were concentrated under reduced pressure, and the resultant residue was dissolved in dichloromethane (500 mL). Excess silica gel was removed by filtration, after which the solvent was removed under reduced pressure to give the pure aminosquarate derivative (21.17 g, 59.4% yield) as a brown powder. The structure of this compound was confirmed by mass spectroscopy and by $^1H$ and $^{13}C$ NMR spectroscopy.

Example 15

Preparation of 4-[[6-[but-2-oxy]-2-[1,1-dimethylethyl]benz[b]-4H-pyran-4-ylidene]methyl]-3-propylaminocyclobut-3-ene-1,2-dione This Example illustrates the preparation, by reactions analogous to those described in Example 14 above, of the aminosquaric acid derivative of Formula II in which $Q^1$ is a 6-[but-2-oxy]-2-[1,1-dimethylethyl]benz[b]-4H-pyran-4-ylidene grouping, $R^3$ is a propyl group, and $R^2$ and $R^4$ are each a hydrogen atom.

Part A: Preparation of 4-[[6-[but-2-oxy]-2-[1,1-dimethylethyl]benz[b]-4H-pyran-4-ylidene]methyl]-3-chlorocyclobut-3-ene-1,2-dione A solution of 6-[but-2-oxy]-2-[1,1-dimethylethyl]-4-methylbenzpyrylium tetrafluoroborate (10.0 g, 27.8 mmol, prepared in Example 39, Part C below) in acetonitrile (70 mL) was added dropwise over a period of 30 minutes to a solution of 3,4-dichlorocyclobut-3-ene-1,2-dione (4.5 g, 29.8 mmol, prepared as described in Schmidt, A. H., Synthesis, 1980, 963) in a mixture of acetonitrile (10 mL) and N-methylpyrrolidone (NMP, 20 mL), with ice/water cooling. A precipitate quickly formed, and stirring became somewhat difficult. The mixture was then allowed to warm to room temperature and stirring was continued for 1 hour, after which the mixture was refrigerated. The product was isolated by filtration, washed with a little cold acetonitrile, and air-dried to give a dark orange powder (6.71 g, 62% yield) which was pure enough for direct use in Part B below. The structure of this compound was confirmed by mass spectroscopy and by $^1$H and $^{13}$C NMR spectroscopy.

Part B: Preparation of 4-[[6-[but-2-oxy]-2-[1,1-dimethylethyl]benz[b]-4H-pyran-4-ylidene]methyl]-3-propylaminocyclobut-3-ene-1,2-dione Propylamine (0.1 mL) was added to a stirred solution of 4-[[6-[but-2-oxy]-2-[1,1-dimethylethyl]benz[b]-4H-pyran-4-ylidene]methyl]-3-chlorocyclobut-3-ene-1,2-dione (2.27 g, 5.9 mmol, prepared in Part A above) in dichloromethane (40 mL) at room temperature, and the mixture was stirred for 17 hours at room temperature, during which time a precipitate formed. Hexanes (50 mL) were then added, and the precipitate was collected by filtration, washed with 1:1 hexanes/dichloromethane (10 mL) and air dried to afford the desired compound (2.3 g, 84% yield) as orange needles. Mass spectroscopy and $^1$H and $^{13}$C NMR spectroscopy showed that the compound was associated with exactly one equivalent of propylamine, possibly in the form of a salt.

EXAMPLES 16–27

Second Process of the Invention

The following Examples 16–27 illustrate the second process of the invention, that is to say reactions analogous to reaction L→A, shown in FIG. 2, together with certain reactions used for the conversion of compounds of Formula I to other compounds of Formula I.

Example 16

Preparation of 4-[[2-amino-3-[[7-diethylamino-2-[1,1-dimethylethyl]benz[b]-4H-pyran-4-ylidene]methyl]-4-oxo-2-cyclobuten-1-ylidene]methyl]-7-diethylamino-2-[1,1-dimethylethyl]benz[b]pyrylium tetrafluoroborate This Example illustrates the preparation, by the reaction L→A shown in FIG. 2, of the dye A in which $R^1$, $R^2$, $R^3$ and $R^4$ are each a hydrogen atom, this being the dye of Formula I in which $Q^1$ is a 2-(1,1-dimethylethyl)-7-diethylaminobenz[b]-4H-pyran-4-ylidene grouping, $Q^2$ is a 4-[2-(1,1-dimethylethyl)-7-diethylaminobenz[b]-4H-pyrylium] grouping, and $R^1$, $R^2$, $R^3$ and $R^4$ are each a hydrogen atom.

A solution of the crude product from Example 5 above, 7-diethylamino-2-[1,1-dimethylethyl]-4-methylbenzpyrylium tetrafluoroborate (prepared as described in the aforementioned copending application U.S. Ser. No. 07/616,639, 250 mg, 0.7 mmol) and quinoline (5 drops) was heated at reflux in butanol (5 mL) for 4 hours, then cooled and allowed to stand overnight. The crude product was separated by filtration and washed with ether to afford green crystals of the dye (161 mg, 37% yield over the two steps of Example 5 and this Example) which had a principal infra-red absorption at 797 nm in dichloromethane solution, $\epsilon$=334,000. The structure of this compound was confirmed by mass spectroscopy and by $^1$H and $^{13}$C NMR spectroscopy.

Examples 17–19

Preparation of Other Dyes

The following dyes were prepared from the aminosquaric acid derivatives of Examples 6–8 respectively above using the same reaction conditions as in Example 16 above.

Example 17

4-[[2-amino-3-[[2,6-bis[1,1-dimethylethyl]thio-4H-pyran-4-ylidene]methyl]-4-oxo-2-cyclobuten-1-ylidene]methyl]-2,6-bis-[1,1-dimethylethyl] thiopyrylium tetrafluoroborate This is the compound of Formula I in which $Q^1$ is a 2,6-bis(1,1-dimethylethyl)-4H-thiopyran-4-ylidene grouping, $Q^2$ is a 4-[2,6-bis-(1,1-dimethylethyl)-4H-thiopyrylium] grouping, and $R^1$, $R^2$, $R^3$ and $R^4$ are each a hydrogen atom. The dye had a principal infra-red absorption at 805 nm in dichloromethane solution, $\epsilon$=224,000. The structure of this compound was confirmed by mass spectroscopy and by $^1$H NMR spectroscopy.

Example 18

4-[[2-amino-3-[1-[2,6-bis[1,1-dimethylethyl]thio-4H-pyran-4-ylidene]eth-1-yl]-4-oxo-2-cyclobuten-1-ylidene]methyl]-2,6-bis-[1,1-dimethylethyl] thiopyrylium tetrafluoroborate This is the compound of Formula I in which $Q^1$ is a 2,6-bis(1,1-dimethylethyl)-4H-thiopyran-4-ylidene grouping, $Q^2$ is a 4-[2,6-bis-(1,1-dimethylethyl)-4H-thiopyrylium] grouping, $R^1$ is a methyl group, and $R^2$, $R^3$ and $R^4$ are each a hydrogen atom. The structure of this compound was confirmed by mass spectroscopy. The impure unsymmetrical dye has a principal infra-red absorption at 834 nm in dichloromethane solution.

Example 19

4-[[2-amino-3-[[2,6-bis[1,1-dimethylethyl]seleno-4H-pyran-4-ylidene]methyl]-4-oxo-2-cyclobuten-1-ylidene]methyl]-2,6-bis-[1,1-dimethylethyl]-selenopyrylium tetrafluoroborate This is the compound of Formula I in which $Q^1$ is a 2,6-bis(1,1-dimethylethyl)-4H-selenopyran-4-ylidene grouping, $Q^2$ is a 4-[2,6-bis-(1,1-dimethylethyl)-4H-selenopyrylium] grouping, and $R^1$, $R^2$, $R^3$ and $R^4$ are each a hydrogen atom. The dye had a principal infra-red absorption at 844 nm in dichloromethane solution, $\epsilon$=287,000. The structure of this compound was confirmed by mass spectroscopy and by $^1$H and $^{13}$C NMR spectroscopy.

Example 20

Preparation of 4-[[3-[[7-diethylamino-2-[1,1-dimethylethyl]benz[b]-4H-pyran-4-ylidene]methyl]-4-oxo-2-pivaloylamino-2-cyclobuten-1-ylidene] methyl]-7-diethylamino-2-[1,1-dimethylethyl]benz [b]pyrylium tetrafluoroborate This Example illustrates the preparation of the dye A in which $R^3$ is a pivaloyl grouping and $R^1$, $R^2$ and $R^4$ are each a hydrogen atom (this being the dye of Formula I in which $Q^1$ is a 2-(1,1-dimethylethyl)-7-diethylaminobenz[b]-4H-pyran-4-ylidene grouping, $Q^2$ is a 4-[2-(1,1-dimethylethyl)-7-diethylaminobenz[b]-4H-pyrylium] grouping, $R^3$ is a pivaloyl grouping and $R^1$, $R^2$ and $R^4$ each a hydrogen atom), from the corresponding dye in which $R^3$ is a hydrogen atom.

1,8-Diazabicyclo[5.4.0]undec-7-ene (DBU, 1 drop, available from the Aldrich Chemical Company, Milwaukee, Wis.) was added to a mixture of 4-[[2-amino-3-[[7-diethylamino-2-[1,1-dimethylethyl]benz[b]-4H-pyran-4-ylidene]methyl]-4-oxo-2-cyclobuten-1-ylidene]methyl]-7-diethylamino-2-[1,1-dimethylethyl]benz[b]pyrylium tetrafluoroborate (10 mg, 0.016 mmol, prepared in Example 16 above) and pivaloyl chloride (5 drops) in dichloromethane (2 mL). Dissolution of the dye starting material was observed over a period of 1 hour, after which the crude reaction mixture was purified directly by preparative thin-layer chromatography on silica gel with 5% methanol/dichloromethane as eluent to afford the desired dye (10 mg, 89% yield); this dye had a principal infra-red absorption at

33

782 nm in dichloromethane solution, ε=282,000. The structure of this dye was confirmed by $^1$H NMR spectroscopy and by mass spectroscopy.

Example 21

Preparation of 4-[[3-[[7-diethylamino-2-[1,1-dimethylethyl]benz[b]-4H-pyran-4-ylidene]methyl-4-oxo-2-[4-methylbenzene-1-sulfonyl]amino-2-cyclobuten-1-ylidene]methyl-7-diethylamino-2-[1,1-dimethylethyl]benz[b]pyrylium hydroxide inner salt dye This Example illustrates the preparation of the dye A (FIG. 2) in which $R^3$ is a toluenesulfonyl grouping and $R^1$, $R^2$ and $R^4$ are each a hydrogen atom (this being the dye of Formula I in which $Q^1$ is a 2-(1,1-dimethylethyl)-7-diethylaminobenz[b]-4H-pyran-4-ylidene grouping, $Q^2$ is a 4-[2-(1,1-dimethylethyl)-7-diethylaminobenz[b]-4H-pyrylium] grouping, $R^3$ is a toluenesulfonyl grouping and $R^1$, $R^2$ and $R^4$ are each a hydrogen atom), from the corresponding dye in which $R^3$ is a hydrogen atom.

A solution of DBU (12 mg 0.078 mmol in dichloromethane (0.5 mL) was added to a mixture of 4-[[2-amino-3-[[7-diethylamino-2-[1,1-dimethylethyl]benz[b]-4H-pyran-4-ylidene]methyl-4-oxo-2-cyclobuten-1-ylidene] methyl-7-diethylamino-2-[1,1-dimethylethyl]benz[b] pyrylium tetrafluoroborate (26 mg, 0.042 mmol, prepared in Example 16 above) and p-toluenesulfonyl chloride (14 mg, 0.073 mmol) in dichloromethane (5 mL). The dark green suspension was converted to a dark brown solution, which was stirred at room temperature for 18 hours, after which time thin-layer chromatography indicated that the reaction was incomplete. More DBU (12 mg) and additional p-toluenesulfonyl chloride were added and stirring was resumed at room temperature and continued for a further 15 days. The reaction was found to be still incomplete at this point, and some undissolved material was present, so dimethylsulfoxide (2 mL) was added and the resultant solution was stirred at room temperature for one day. The reaction mixture was then worked up by pouring it into 1M hydrochloric acid and extracting the resultant mixture with dichloromethane. The organic layer was dried over magnesium sulfate and concentrated under reduced pressure to yield a residue which was purified by preparative thin-layer chromatography with 2% methanol/dichloromethane as eluent to give the dye (6.1 mg, 19% yield) as a green solid; this dye had a principal infra-red absorption at 814 nm in dichloromethane solution, ε=264,000. The structure of this compound was confirmed by mass spectroscopy and by $^1$H and $^{13}$C NMR spectroscopy.

Example 22

Preparation of 4-[[2-diethylamino-3-[[7-diethylamino-2-[1,1-dimethylethyl]benz[4H-pyran-4-ylidene]methyl]-4-oxo-2-cyclobuten-1-ylidene] methyl]-7-diethylamino-2-[1,1-dimethylethyl]benz [b]pyrylium tetrafluoroborate This Example illustrates the preparation, by the reaction L→A shown in FIG. 2, of the dye A in which $R^3$ and $R^4$ are each an ethyl group and $R^1$ and $R^2$ are each a hydrogen atom, this being the dye of Formula I in which $Q^1$ is a 2-(1,1-dimethylethyl)-7-diethylaminobenz[b]-4H-pyran-4-ylidene grouping, $Q^2$ is a 4-[2-(1,1-dimethylethyl)-7-diethylaminobenz[b]-4H-pyrylium] grouping, $R^3$ and $R^4$ are each an ethyl group and $R^1$ and $R^2$ are each a hydrogen atom.

34

A solution of the aminosquaric acid derivative prepared in Example 9 above (70 mg, 0.17 mmol), 7-diethylamino-2-[1,1-dimethylethyl]-4-methylbenzpyrylium tetrafluoroborate (61 mg, 0.17 mmol) and quinoline (22 mg, 0.17 mmol) was heated at reflux in butanol (5 mL) for 24 hours, after which time more 7-diethylamino-2-[1,1-dimethylethyl]-4-methylbenzpyrylium tetrafluoroborate (60 mg, 0.17 mmol) was added, and reflux was resumed for a further 8 hours. The reaction mixture was concentrated under reduced pressure, and the crude product was purified by flash chromatography on silica gel with 5% methanol/dichloromethane as eluent, followed by preparative thin-layer chromatography on silica gel with the same eluent mixture. Dark red crystals (18 mg, 14% yield) were obtained. The dye had a principal infra-red absorption at 828 nm in dichloromethane solution, ε=315,000. The structure of this compound was confirmed by mass spectroscopy and by $^1$H and $^{13}$C NMR spectroscopy.

Examples 23 and 24

Preparation of Other Dyes

The following dyes were prepared from the indicated aminosquaric acid derivatives using the same reaction conditions as in Example 22 above.

Example 23

4-[[2-butylamino-3-[[7-diethylamino-2-[1,1-dimethylethyl]benz[b]-4H-pyran-4-ylidene]methyl]-4-oxo-2-cyclobuten-1-ylidene]methyl]-7-diethylamino-2-[1,1-dimethylethyl]benz[b]-pyrylium tetrafluoroborate This is the dye A in which $R^3$ is a butyl group and $R^1$, $R^2$ and $R^4$ are each a hydrogen atom, this being the dye of Formula I in which $Q^1$ is a 2-(1,1-dimethylethyl)-7-diethylaminobenz[b]-4H-pyran-4-ylidene grouping, $Q^2$ is a 4-[2-(1,1-dimethylethyl)-7-diethylaminobenz[b]-4H-pyrylium] grouping, $R^3$ is a butyl group and $R^1$, $R^2$ and $R^4$ are each a hydrogen atom. This dye, which was prepared simply by substituting the aminosquaric acid derivative prepared in Example 10 above in the reaction of Example 22, had a principal infra-red absorption at 810 nm in dichloromethane solution, and its structure was confirmed by mass spectroscopy and by $^1$H NMR spectroscopy.

Example 24

4-[[2-propylamino-3-[[2,6-bis[1,1-dimethylethyl] seleno-4H-pyran-4-ylidene]methyl]-4-oxo-2-cyclobuten-1-ylidene]methyl]- 2,6-bis-[1,1-dimethylethyl]selenopyrylium tetrafluoroborate This is the dye of Formula I in which $Q^1$ is a 2,6-bis-(1,1-dimethylethyl)-4H-selenopyran-4-ylidene grouping, $Q^2$ is a 4-[2,6-bis(1,1-dimethylethyl)-4H-selenopyrylium] grouping, $R^3$ is a propyl group, and $R^1$, $R^2$ and $R^4$ are each a hydrogen atom. The starting materials used were the aminosquaric acid derivative prepared in Example 12 above, and the selenopyrylium salt used as starting material in Example 4 above. The dye had a principal infra-red absorption at 860 nm in dichloromethane solution. The structure of this compound was confirmed by mass spectroscopy.

Example 25

Preparation of 4-[[2-[3-sulfonatoeth-1-ylamino]-3-[ [7-diethylamino-2-[1,1-dimethylethyl]benz[b]-4H-pyran-4-ylidene]methyl]-4-oxo-2-cyclobuten-1-ylidene]methyl]-7-diethylamino-2-[1,1-dimethylethyl]benz[b]pyrylium inner salt dye This Example illustrates the preparation, by the reaction L→A shown in FIG. 2, of the dye A in which $R^3$ is (notionally) a —CH$_2$CH$_2$SO$_3$H grouping, and R$^1$, R$^2$, and R$^4$ are each a hydrogen atom, this being the dye of Formula I in which Q$^1$ is a 2-(1,1-dimethylethyl)-7-diethylaminobenz[b]-4H-pyran-4-ylidene grouping, Q$^2$ is a 4-[2-(1,1-dimethylethyl)-7-diethylaminobenz[b]-4H-pyrylium] grouping, R$^3$ is (notionally) a —CH$_2$CH$_2$SO$_3$H grouping, and R$^1$, R$^2$ and R$^4$ are each a hydrogen atom.

A solution of the orange material prepared in Example 13 above, (70 mg, 0.13 mmol), 7-diethylamino-2-[1,1-dimethylethyl]-4-methylbenzpyrylium tetrafluoroborate (50 mg, 0.14 mmol) and quinoline (17 mg, 0.13 mmol) was heated at reflux in butanol (5 mL) for 5 hours, then cooled and allowed to stand overnight at 5° C. The crude product was separated by filtration and washed with ether to afford red crystals of the dye (36 mg, 38% yield) which had a principal infra-red absorption at 814 nm in dichloromethane solution, ε=333,000. The structure of this dye was confirmed by mass spectroscopy and by $^1$H NMR spectroscopy.

Example 26

Preparation of 6-[but-2-oxy]-4-[[3-[[2-[1,1-dimethylethyl]-6-methoxybenz[b]-4H-thiopyran-4-ylidene]methyl]-4-oxo-2-[propylamino]-2-cyclobuten-1-ylidene]methyl]-2-[1,1-dimethylethyl]benz[b]pyrylium tetrafluoroborate This Example illustrates the preparation of the dye of Formula I in which Q$^1$ is a 2-[1,1-dimethylethyl]-6-methoxybenz[b]-4H-thiopyran-4-ylidene grouping Q$^2$ is a 6-[but-2-oxy]-2-[1,1-dimethylethyl]benz[b]pyrylium grouping, R$^3$ is a propyl group and R$^1$, R$^2$ and R$^4$ are each a hydrogen atom. In this Example, the aminosquaric acid derivative of Formula II contains the benzthiopyrylium nucleus, and the reaction is promoted with a Lewis acid, namely titanium tetrachloride.

Titanium tetrachloride (8 mL of a 1M solution in dichloromethane, 8 mmole) was added to a solution of 4-[[2-[1,1-dimethylethyl]-6-methoxybenz[b]-4H-thiopyran-4-ylidene]methyl]-3-propylaminocyclobut-3-ene-1,2-dione (1.0 g, 2.6 mmol, prepared in Example 14 above), 6-[but-2-oxy]-2-[1,1-dimethylethyl]-4-methylbenzpyrylium tetrafluoroborate (1.0 g, 2.8 mmole, prepared in Example 39 below) and quinoline (2.8 g, 22 mmole) in dichloromethane (150 mL) at room temperature under nitrogen, and the mixture was stirred at room temperature for 2 hours. The mixture was then washed sequentially with 200 mL quantities of:

i) water containing tetrafluoroboric acid (10 mL of a 48% aqueous solution);
ii) water;
iii) 10% aqueous sodium hydrogen carbonate solution;
iv) water; and
v) 10% aqueous sodium tetrafluoroborate solution.

The organic layer was then dried over anhydrous sodium sulfate and concentrated. The residue was partially purified by flash chromatography on silica gel with 0–2% methanol/dichloromethane as eluent. Further purification was effected by stirring the chromatographed material with methyl t-butyl ether (MTBE) (5 mL), storing the resultant suspension in a freezer (at about 5° C.) for 17 hours, removing the solvent by decantation and triturating the residue with hexanes (25 mL). Air-drying following this purification afforded a brown powder, which still contained impurities. Final purification was achieved by stirring the brown powder for 5 minutes in a mixture of acetone (5 mL) and hexanes (10 mL). The brown, suspended material was collected by filtration, washed with a further small amount of 1:2 acetone/hexanes, and air dried to afford the dye (0.47 g, 25% yield). The dye had an absorption in the near infra-red in dichloromethane solution at 848 nm, ε=230,000. The structure of this compound was confirmed by mass spectroscopy and by $^1$H and $^{13}$C NMR spectroscopy.

Example 27

Preparation of 6-[but-2-oxy]-4-[[3-[[2-[1,1-dimethylethyl]-6-methoxybenz[b]-4H-thiopyran-4-ylidene]methyl]-4-oxo-2-[propylamino]-2-cyclobuten-1-ylidene]methyl]-2-[1,1-dimethylethyl]benz[b]pyrylium tetrafluoroborate This Example illustrates the preparation of the same dye as in Example 26 above, but starting from an aminosquaric acid derivative of Formula II containing the benzpyrylium nucleus. Again, the reaction is promoted with a Lewis acid, namely titanium tetrachloride.

Titanium tetrachloride (3 mL of a 1M solution in dichloromethane, 3 mmol) was added over a period of 30 seconds to a solution of 6-[but-2-oxy]-4-[[2-1,1-dimethylethyl]benz[b]-4H-pyran-4-ylidene]methyl]-3-propylaminocyclobut-3-ene-1,2-dione (0.41 g, 1 mmol, prepared in Example 15 above), 2-[1,1-dimethylethyl]-6-methoxy-4-methylbenzthiopyrylium tetrafluoroborate (0.36 g, 1.1 mmol, prepared in Example 32 below) and quinoline (1.1 g, 8.5 mmol) in dichloromethane (35 mL) at room temperature under nitrogen. The mixture was stirred at room temperature for 2 hours, then washed sequentially with 50 mL quantities of:

i) water containing tetrafluoroboric acid (2 mL of a 48% aqueous solution);
ii) water;
iii) water containing sodium hydrogen carbonate (3 g);
iv) water; and
v) water containing sodium tetrafluoroborate (3 g).

The organic layer was then dried over anhydrous sodium sulfate and concentrated. The residue was partially purified by trituration with 2:1 hexanes/acetone (15 mL). Collection of the solid remaining after trituration by filtration, followed by washing with a further small amount of 2:1 hexanes/acetone afforded the dye as a coppery powder (0.22 g, 30% yield). This material was spectroscopically identical to the material prepared in Example 26 above.

EXAMPLE 28

Third Process of the Invention

The following Example 28 illustrates the third process of the invention, that is to say the preferred reaction for the preparation of the sulfonamide dyes of the invention.

Example 28

Preparation of 4-[[3-[[2,6-bis[1,1-dimethylethyl]thio-4H-pyran-4-ylidene]methyl]-2-butanesulfonylamino-4-oxo-2-cyclobuten-1-ylidene]methyl]-2,6-bis-[1,1-dimethylethyl]thiopyrylium hydroxide inner salt dye This Example illustrates the preparation of a dye of Formula I, in which Q$^1$ is a 2,6-bis(1,1-dimethylethyl)-4H-thiopyran-4-ylidene grouping, Q$^2$ is a 4-[2,6-bis(1,1-dimethylethyl)-4H-thiopyrylium] grouping, R$^3$ is a CH$_3$CH$_2$CH$_2$CH$_2$SO$_2$— grouping, and R$^1$, R$^2$ and R$^4$ are each a hydrogen atom, starting from the corresponding dye in which the squarylium nucleus is unsubstituted.

Butanesulfonyl isocyanate (3 drops, approx. 30 mg) was added to a solution of 4-[[3-[[2,6-bis[1,1-dimethylethyl] thio-4H-pyran-4-ylidene]methyl]-2-hydroxy-4-oxo-2-cyclobuten-1-ylidene]methyl]-2,6-bis[1,1-dimethylethyl] thiopyrylium hydroxide inner salt dye (100 mg, 0.19 mmol, prepared as described in U.S. Pat. No. 4,508,811) in toluene (15 mL) and the reaction mixture was heated to 95° C. for 2 hours. Additional butanesulfonyl isocyanate (3 drops) was added and heating was continued for a further 2 hours. A final addition of butanesulfonyl isocyanate (3 drops) then took place, followed by heating for 2 more hours. The reaction mixture was then diluted with ether and washed with water. The organic layer was dried over sodium sulfate and concentrated under reduced pressure, then the residual dark green oil produced was purified by flash chromatography on silica gel. The material which eluted first from the column was the dye (3.4 mg, 3% yield) which had a principal infra-red absorption at 828 nm in dichloromethane solution. The structure of this compound was confirmed by $^1$H NMR spectroscopy and mass spectroscopy.

EXAMPLES 29–37

Fourth Process of the Invention

The following Examples 29–37 illustrate the fourth process of the invention, that is to say reactions analogous to Q→R shown in FIG. 3, together with reactions analogous to P→Q shown in FIG. 3 and certain other reactions necessary for the preparation of starting materials.

Example 29

Preparation of 4-butylamino-3-ethoxycyclobut-3-ene-1,2-dione

This Example illustrates the preparation, by the reaction P→Q shown in FIG. 3, of the aminosquaric acid derivative Q in which $R^3$ is a butyl group and $R^4$ is a hydrogen atom.

Butylamine (86 mg, 1.18 mmol) was added to a solution of diethyl squarate (200 mg, 1.18 mmol) in dichloromethane (5 mL) at room temperature, and the reaction mixture was stirred for one hour. The slightly cloudy mixture was then filtered and evaporated to give the desired aminosquaric acid derivative as a yellowish solid (216 mg, 93% yield). The structure of this compound was confirmed by mass spectroscopy and by $^1$H and $^{13}$C NMR spectroscopy.

Example 30

Preparation of 4-[[2-butylamino-3-[[2,6-bis[1,1-dimethylethyl]thiopyran-4-ylidene]methyl]-4-oxo-2-cyclobuten-1-ylidene]methyl]-2,6-bis[1,1-dimethylethyl]thiopyrylium tetrafluoroborate This Example illustrates the preparation, by the reaction Q+R→N shown in FIG. 3, of the dye Q in which $R^3$ is a butyl group and $R^1$, $R^2$ and $R^4$ are each a hydrogen atom, this being the dye of Formula I in which $Q^1$ is a 2,6-bis(1,1-dimethylethyl)-4H-thiopyran-4-ylidene grouping, $Q^2$ is a 4-[2,6-bis(1,1-dimethylethyl)-4H-thiopyrylium] grouping, $R^3$ is a butyl group and $R^1$, $R^2$ and $R^4$ are each a hydrogen atom.

4-Butylamino-3-ethoxycyclobut-3-ene-1,2-dione (prepared in Example 29 above, 50 mg, 0.25 mmol), 2,6-bis[1,1-dimethylethyl]-4-methylthiopyrylium tetrafluoroborate (see U.S. Pat. No. 4,343,948, 155 mg, 0.5 mmol) and quinoline (150 mg, 1.18 mmol) were heated at reflux in butanol (5 mL) for one hour. The reaction mixture was then held at room temperature overnight, after which it was heated at reflux for a further 2 hours. The solvent was removed under reduced pressure and the residue was triturated with ether. The ether extracts, which contained the dye, were concentrated and the crude material was partially purified by preparative thin-layer chromatography on silica gel with 7% methanol/dichloromethane as eluent. Repeating the chromatographic purification gave the dye (3.2 mg, 2% yield) as a brown glass. The dye exhibited a principal infra-red absorption at 816 nm in dichloromethane solution, ∈=135,000. The structure of this dye was confirmed by mass spectroscopy and by $^1$H and $^{13}$C NMR spectroscopy.

Examples 31–33

Preparation of 4-[[3-[[2-[1,1-dimethylethyl]-6-methoxybenz[b]-4H-thiopyran-4-ylidene]methyl]-4-oxo-2-[propylamino]-2-cyclobuten-1-ylidene] methyl]-2-[1,1-dimethylethyl]-6-methoxybenz[b] thiopyrylium tetrafluoroborate These Examples illustrate the preparation of the dye of Formula I in which $Q^1$ is a 2-[1,1-dimethylethyl]-6-methoxybenz[b]-4H-thiopyran-4-ylidene grouping, $Q^2$ is a 2-[1,1-dimethylethyl]-6-methoxybenz[b]-thiopyrylium grouping, $R^3$ is a propyl group and $R^1$, $R^2$ and $R^4$ are each a hydrogen atom.

Example 31

Preparation of 2-[butoxy]-4-[propylamino]cyclobut-3-ene-1,2-dione

This Example illustrates a reaction analogous to P→Q shown in FIG. 3, but which produces the butyl homologue of the compound P in which the $NR^3R^4$ is a propylamino group.

A solution of propylamine (26 mL, 0.31 mmol) in ether (100 mL) was added to a solution of dibutyl squarate (57.68 g, 0.255 mmol) in ether (300 mL), and the mixture was allowed to stand at room temperature for two hours, then filtered and the filtrate concentrated under reduced pressure to yield a yellow, oily solid (52.46 g, 97.5% yield). The structure of this compound was confirmed by mass spectroscopy and by $^1$H and $^{13}$C spectroscopy.

Example 32

Preparation of 2-[1,1-dimethylethyl]-6-methoxy-4-methylbenz[b]thiopyrylium tetrafluoroborate This Example illustrates the preparation of the 6-methoxy-7-unsubstituted thiopyrylium analogue of the compound M shown in FIG. 2 in which $R^2$ is a hydrogen atom (i.e., the 4-substituent is a methyl group).

Part A: Preparation of ethyl 4,4-dimethylpent-2-ynoate

This is an improved preparation of a compound described in E. A. Halohen, Acta Chem. Scand., 9, 1492–1497 (1955).

t-Butylacetylene (15.38 g, 0.188 mol) was dissolved in tetrahydrofuran (100 mL) in a 500 mL three-necked round-bottomed flask fitted with a nitrogen bubbler, rubber septum and dropping funnel. The resultant solution was cooled to −70° C. using a dry ice/acetone bath, and butyl lithium (72 mL of a 2.5M solution in hexanes, 0.18 mol) was added dropwise via a syringe. The cooling bath was then removed and the reaction mixture was stirred for 30 minutes, during which time the temperature in the flask rose to 10°–15° C. The flask was then again cooled to –70° C. and a solution of ethyl chloroformate (19.5 g, 0.18 mol) was added dropwise. The cooling bath was again removed, and the reaction mixture was stirred for 3 hours. Cold water (75 mL) was next added to quench the reaction, and the aqueous and organic phases were separated. The aqueous phase was extracted with THF (50 mL) and the combined organic phases were washed with 0.1M hydrochloric acid (75 mL) and brine (100 mL), and dried over magnesium sulfate. Removal of the solvent under reduced pressure afforded a pale yellow oil (28 g) which was distilled under reduced pressure to provide the propiolate ester (23.5 g, 85% yield) as a colorless liquid which boiled at 70°–75° C. at 18–20 mm Hg. The structure of this compound was confirmed by mass spectroscopy and by $^1$H and $^{13}$C NMR spectroscopy.

Part B: Preparation of 4-dimethyl-3-(4-methoxyphenylthio)pent-2-enoic acid

This and the next step are modifications of the methods described in M. R. Detty and B. J. Murray, J. Am. Chem. Soc., 105, 883–890 (1983).

A solution of 4-methoxybenzene thiol (14.0 g, 0.1 mol) in methanol (25 mL) was added in one portion to sodium methoxide (21.6 g of a 25% solution in methanol, 0.1 mol) with ice/water bath cooling. The flask was warmed to room temperature, stirred for 15 minutes, and then cooled again using the ice/water bath. A solution of ethyl 4,4-dimethylpent-2-ynoate (15.4 g, 0.1 mol, prepared in Part A above) in methanol (25 mL) was next added in one portion. The reaction mixture was warmed to room temperature, stirred for one hour, and then diluted with ethanol (95%, 75 mL). Potassium hydroxide (30 mL of a 40% aqueous solution) was added, and the resultant solution was heated to 50°–60° C. using a water bath, and stirred at this temperature for 2 hours. The mixture was then cooled to room temperature and diluted with cold water (circa 400 mL). The resultant cloudy suspension was extracted with carbon tetrachloride (3×100 mL) and the aqueous layer was acidified with ice-cold 6M hydrochloric acid (to about pH 3), whereupon a precipitate of the desired carboxylic acid separated. The product was extracted with dichloromethane (3 100 mL aliquots), and the solution was dried over magnesium sulfate. Removal of solvent under reduced pressure afforded the acid (21.4 g, 80% yield) as a white solid. The structure of this compound was confirmed by mass spectroscopy and by $^1$H and $^{13}$C NMR spectroscopy.

Part C: Preparation of 2-[1,1-dimethylethyl]-6-methoxybenz[b]-4H-thiopyran-4-one Methanesulfonic acid (2.6 g, 27 mmol) was added to a suspension of 4-dimethyl-3-(4-methoxyphenylthio)pent-2-enoic acid (6.72 g, 25 mmol, prepared in Part B above) in acetic anhydride (20 mL). The reaction flask was then stirred and heated with a pre-heated oil bath at 80°–85° C. for about 30 minutes, during which time the color of the reaction mixture changed from brown to deep green. The mixture was then cooled and the reaction was quenched by addition of crushed ice/water (50 g). The resultant mixture was stirred for 20 minutes, then extracted with hexanes (5 50 mL aliquots). The combined hexane extracts were washed with a saturated aqueous solution of sodium hydrogen carbonate and with brine, and dried over magnesium sulfate. Removal of solvent under reduced pressure afforded the thiochromone (5.74 g). $^1$H NMR indicated that the material was almost pure, so this material was used without further purification in the reaction of Part D below.

Part D: Preparation of 2-[1,1-dimethylethyl]-6-methoxy-4-methylbenz[b]thiopyrylium tetrafluoroborate Methyl magnesium bromide (50 mL of a 3M solution in ether, 0.15 mmol) was added to a solution of the crude thiochromone (20 g, prepared in Part C above) in THF (100 mL) with cooling to 10° C. The reaction mixture was then allowed to warm to room temperature and stirred for 6 hours. The mixture was then added, with vigorous stirring, to tetrafluoroboric acid (125 mL of a 50% aqueous solution) which had been diluted with ice/water (600 mL). A yellow precipitate formed, which was collected by vacuum filtration, washed thoroughly with hexanes and dried under reduced pressure to yield the desired salt (18.5 g, 55% yield over three steps from the 4-methoxybenzene thiol). The structure of this compound was confirmed by mass spectroscopy and by $^1$H and $^{13}$C NMR spectroscopy.

Example 33

Preparation of 4-[[3-[[2-[1,1-dimethylethyl]-6-methoxybenz[b]-4H-thiopyran-4-ylidene]methyl]-4-oxo-2-[propylamino]-2-cyclobuten-1-ylidene] methyl]-2-[1,1-dimethylethyl]-6-methoxybenz[b] thiopyrylium tetrafluoroborate A solution of 2-[butoxy]-4-[propylamino]-cyclobut-3-ene-1,2-dione (5.16 g, 24.4 mmol, prepared in Example 31 above) in dichloromethane (100 mL) was placed in a 2 L, three-necked round-bottomed flask equipped with a mechanical stirrer, under a nitrogen atmosphere. The flask was then charged with a suspension of 2-[1,1-dimethylethyl]-6-methoxy-4-methylbenzthiopyrylium tetrafluoroborate (8.17 g, 24.4 mmol, prepared in Example 32 above) in dichloromethane (400 mL), followed by a solution of quinoline (25.1 g, 0.2 mol) in dichloromethane (50 mL), and finally by a solution of titanium tetrachloride (26.7 mL of a 1M solution in dichloromethane, added using a syringe); a somewhat exothermic reaction followed the final addition. The resultant reaction mixture was stirred for 17 hours, after which time tetrafluoroboric acid (150 mL of a 55% aqueous solution) was added. After a further one hour's stirring, the mixture was extracted with water (2 100 mL aliquots), and the dichloromethane layer was washed with saturated sodium bicarbonate solution (2 100 mL aliquots) and saturated sodium tetrafluoroborate solution (2 100 mL aliquots), dried, and concentrated under reduced pressure. The crude material thus obtained was dissolved in dichloromethane (50 mL) and precipitated with MTBE (400 mL). Repeating this procedure provided the dye as a red-brown solid (5.21 g, 61% yield). The dye exhibited a near infra-red absorption in dichloromethane solution at 902 nm, $\epsilon$=218,000. The structure of this compound was confirmed by mass spectroscopy and by $^1$H and $^{13}$C NMR spectroscopy.

Examples 34 and 35

Preparation of 4-[[2-[but-2-ylamino]-3-[[2-[1,1-dimethylethyl]-6-methoxybenz[b]-4H-thiopyran-4-ylidene]methyl]-4-oxo-2-cyclobuten-1-ylidene] methyl]-2-[1,1-dimethylethyl]-6-methoxybenz[b] thiopyrylium tetrafluoroborate These Examples illustrate the preparation of the dye of Formula I in which $Q^1$ is a 2-[1,1-dimethylethyl]-6-methoxybenz[b]-4H-thiopyran-4-ylidene grouping, $Q^2$ is a 2-[1,1-dimethylethyl]-6-methoxybenz[b]thiopyrylium grouping, $R^3$ is an but-2-yl group and $R^1$, $R^2$ and $R^4$ are each a hydrogen atom.

Example 34

Preparation of 2-[butoxy]-4-[but-2-ylamino]-cyclobut-3-ene-1,2-dione

This Example illustrates a reaction analogous to P→Q shown in FIG. 3, but which produces the butyl homologue of the compound P in which the $NR^3R^4$ is a but-2-ylamino group.

sec-Butylamine (8.89 g, 0.122 mol) was added dropwise to a solution of dibutyl squarate (25.0 g, 0.11 mol) in ether (100 mL) under a nitrogen atmosphere, with ice bath cooling, over a period of 10 minutes. The resultant yellow solution was stirred at room temperature for 16 hours, after which time the solvent was removed under reduced pressure. Trituration with hexanes yielded the desired amine as a waxy solid, which was dried under a stream of nitrogen to give 27.25 g of product (contaminated with a trace of butanol). The structure of this compound was confirmed by $^1H$ and $^{13}C$ NMR spectroscopy.

Example 35

Preparation of 4-[[2-[but-2-ylamino]-3-[[2-[1,1-dimethylethyl]-6-methoxybenz[b]-4H-thiopyran-4-ylidene]methyl]-4-oxo-2-cyclobuten-1-ylidene] methyl]-2-[1,1-dimethylethyl]-6-methoxybenz[b] thiopyrylium tetrafluoroborate Titanium tetrachloride (30 mL of a 1M solution in dichloromethane, 0.03 mol) was added, over a period of 5 minutes, at room temperature under nitrogen, to a solution of 2-[1,1-dimethylethyl]-6-methoxy-4-methylbenz[b] thiopyrylium tetrafluoroborate (3.75 g, 0.0112 mol, prepared in Example 32 above), 2-butoxy-4-[but-2-ylamino]-cyclobut-3-ene-1,2-dione (2.55 g, 0.0113 mol, prepared in Example 34 above) and quinoline (18.0 g, 0.14 mol) in dichloromethane (250 mL). The resultant mixture was stirred for 4 hours, after which time tetrafluoroboric acid (50 mL of a 48% aqueous solution) was added, followed by water (100 mL). The layers were separated, and the organic phase was washed successively with 100 mL portions of water, water (100 mL) containing sodium hydrogen carbonate (10 g), water, and water (100 mL) containing sodium tetrafluoroborate (10 g). The washed organic phase was then dried over sodium sulfate and concentrated under reduced pressure to give a black residue which was triturated with 20 mL of a 3:1 hexanes/acetone mixture at 0° C. The solid was collected, washed with a further small portion of the cold triturating solution, and dried to afford the dye (2.75 g, 69% yield) as a dark brown powder, having an absorption maximum in dichloromethane solution at 902 nm, $\epsilon=179,200$. The structure of this compound was confirmed by mass spectroscopy and by $^1H$ and $^{13}C$ NMR spectroscopy.

Examples 36 and 37

Preparation of 4-[[2-[but-2-ylamino]-3-[[6-[2-ethylbut-1-oxy]-2-phenylbenz[b]-4H-pyran-4-ylidene]methyl]-4-oxo-2-cyclobuten-1-ylidene] methyl]-6-[2-ethylbut-1-oxy]-2-phenylbenz[b] pyrylium tetrafluoroborate These Examples illustrate the preparation of the dye of Formula I in which $Q^1$ is a 6-[2-ethylbut-1-oxy]-2-phenylbenz[b]-4H-pyran-4-ylidene grouping, $Q^2$ is a 6-[2-ethylbut-1-oxy]-2-phenylbenz[b]pyrylium grouping, $R^3$ is an but-2-yl group and $R^1$, $R^2$ and $R^4$ are each a hydrogen atom.

Example 36

Preparation of 6-[2-ethylbut-1-oxy]-4-methyl-2-phenylbenzpyrylium tetrafluoroborate This Example illustrates the preparation of the 2-phenyl-4-methyl-6-[2-ethylbut-1-oxy] 7-unsubstituted analogue of the benzpyrylium salt B shown in FIG. 1.

Part A: Preparation of 6-hydroxy-2-phenylbenz-4H-pyran-4-one

Trifluoromethanesulfonic acid (20 mL) was added dropwise, with stirring, to a mixture of hydroquinone (3.3 g, 0.03 mol) and ethyl 3-oxo-3-phenylpropanoate (6.3 g, 0.033 mol). The dark red resultant solution was stirred at room temperature for 2 hours, then heated to 60° C. for a further 2 hours, cooled and poured slowly into water (250 mL). The mixture so formed was stirred, and the solid product which precipitated was collected by filtration, washed with water, and recrystallized from methanol (250 mL) to yield the desired chromone as cream-colored platelets (4.2 g, 59% yield). The structure of this compound was confirmed by mass spectroscopy and by $^1H$ and $^{13}C$ NMR spectroscopy.

Part B: Preparation of 6-[2-ethylbut-1-oxy]-2-phenylbenz-4H-pyran-4-one

A mixture of 6-hydroxy-2-phenylbenz-4H-pyran-4-one (1.2 g, 5 mmol, prepared in Part A above), 1-bromo-2-ethylbutane (1.03 g, 7.5 mmol), potassium carbonate (1.04 g, 7.5 mmol) and sodium iodide (0.75 g, 5 mmol) in methyl ethyl ketone (MEK, 10 mL) was heated for 17 hours at reflux under nitrogen. At this point thin layer chromatography indicated that the reaction was incomplete, so a further quantity of 1-bromo-2-ethylbutane (1.03 g, 7.5 mmol) was added, and heating was resumed for a further 8 hours. To drive the reaction to completion, a final quantity of 1-bromo-2-ethylbutane (1.03 g, 7.5 mmol) was then added, and heating was continued for another 17 hours. The reaction mixture was poured into water (250 mL), and the resultant mixture was acidified using concentrated hydrochloric acid, causing an oil to separate. The mixture was extracted with ether (2 50 mL aliquots), and the organic layers were washed with water (150 mL), dried over sodium sulfate, and concentrated under reduced pressure to yield the product as a yellowish oil which solidified when scratched (1.6 g). The slightly impure material, whose structure was confirmed by $^1H$ and $^{13}C$ NMR spectroscopy, was used directly in Part C below.

Part C: Preparation of 6-[2-ethylbut-1-oxy]-4-methyl-2-phenylbenzpyrylium tetrafluoroborate Methyl magnesium bromide (2 mL of a 3M solution in ether, 6 mmol) was added to a solution of 6-[2-ethylbut-1-oxy]-2-phenylbenz-4H-pyran-4-one (0.75 g, 2.5 mmol, prepared in Part B above) in THF (7.5 mL) at room temperature. An exothermic reaction accompanied the addition. The reaction mixture was allowed to stand at room temperature for 17 hours, and then poured into a stirred solution of tetrafluoroboric acid (7 mL of an 8M solution, diluted with ice/water (200 mL)). Much foaming was observed, and a yellow/green precipitate was formed. The solid material was collected by filtration, washed with water and air dried to afford the desired salt (0.875 g, 92% yield) as a green powder. The structure of this compound was confirmed by mass spectroscopy and by $^1H$ and $^{13}C$ NMR spectroscopy.

Example 37

Preparation of 4-[[2-[but-2-ylamino]-3-[[6-[2-ethylbut-1-oxy]-2-phenylbenz[b]-4H-pyran-4-ylidene]methyl]-4-oxo-2-cyclobuten-1-ylidene] methyl]-6-[2-ethylbut-1-oxy]-2-phenylbenz[b] pyrylium tetrafluoroborate Titanium tetrachloride (0.8 mL of a 1M solution in dichloromethane, 0.8 mmol) was added dropwise via a syringe to a solution of 6-[2-ethylbut-1-oxy]-4-methyl-2-phenylbenzpyrylium tetrafluoroborate (190 mg, 0.5 mmol, prepared in Example 36 above), 2-butoxy-4-[but-2-ylamino]-cyclobut-3-ene-1,2-dione (112 mg, 0.5 mmol, prepared in Example 34 above) and quinoline (510 mg, 4 mmol) in dichloromethane (5 mL) at room temperature under nitrogen. The dark olive-green solution was stirred for 20 minutes, after which time tetrafluoroboric acid (5 mL of an 8M solution) was added and the reaction mixture was stirred for a further 17 hours. Water (10 mL) was then added, the organic layer was separated, and the aqueous layer was extracted with dichloromethane. The combined dichloromethane layers were concentrated under reduced pressure to give a dark green residue, which was stirred with acetone (5 mL) for 10 minutes, precipitating the product. The dye was collected by filtration and washed with acetone to give a dark green solid (126 mg, 58 yield). The dye exhibited a near infra-red absorption in dichloromethane solution at 856 nm, $\epsilon$=201,200. The structure of this compound was further confirmed by mass spectroscopy.

EXAMPLES 38 and 39

The following two Examples illustrate the fourth process of the invention carried out with promotion by a Lewis acid.

Example 38

Preparation of 4-[[2-amino-3-[[2,6-bis-[1,1-dimethylethyl]seleno-4H-pyran-4-ylidene]methyl]-4-oxo-2-cyclobuten-1-ylidene]methyl]-2,6-bis-[1,1-dimethylethyl]selenopyrylium tetrafluoroborate This Example illustrates the preparation of the same dye as in Example 19 above but using trimethylsilyl chloride as a Lewis acid promoter of the condensation which produces the final dye.

Part A: Preparation of 4-amino-3-[but-1-oxy]cyclobut-3-ene-1,2-dione

Ammonia gas was bubbled into a solution of dibutyl squarate (22.6 g, 100 mmol) in ether (500 mL) contained in a 1 L three-necked, round-bottomed flask equipped with a mechanical stirrer and an acidic scrubber. Precipitation of product ceased after 3 hours, so the reaction was halted and the ether solution was filtered. The solid residue was washed with ether and set aside. The filtrate was allowed to stand at room temperature for a further 3 hours, after which time more solid was observed to have been precipitated. This solid was collected by filtration, washed with ether, and combined with the material set aside previously. Drying in vacuo afforded the product as a white solid (15.7 g, 92.9% yield). The structure of this compound was confirmed by mass spectroscopy and by $^1$H and $^{13}$C NMR spectroscopy.

Part B: Preparation of 4-[[2-amino-3-[[2,6-bis-[1,1-dimethylethyl]seleno-4H-pyran-4-ylidene]methyl]-4-oxo-2-cyclobuten-1-ylidene]methyl]-2,6-bis[1,1-dimethylethyl]selenopyrylium tetrafluoroborate Dichloromethane (100 mL), quinoline (12.9 g, 100 mmol), trimethylsilyl chloride (5.44 g, 50 mmol) and 4-amino-3-butoxycyclobut-3-ene-1,2-dione (1.69 g, 10 mmol, prepared in Part A above) were added sequentially to a 250 mL three-necked round-bottomed flask containing 2,6-bis-[1,1-dimethylethyl]-4-methylselenopyrylium tetrafluoroborate (8.93 g, 25 mmol, prepared as described in the aforementioned copending application Ser. No. 07/696,222) under a nitrogen atmosphere. The reaction mixture was heated at reflux for 17 hours, then quenched into a cold solution of tetrafluoroboric acid (20 mL, 48% aqueous solution). The organic layer was separated, washed with water (2 50 mL aliquots), and dried over anhydrous magnesium sulfate, then concentrated under reduced pressure to approximately 50 mL, and poured into a beaker containing diethyl ether (500 mL). The resultant solid was filtered, rinsed with ether and dried in vacuo to afford 5.7 g of the crude product as a dark brick-red solid. Fractional crystallization by addition of t-butyl methyl ether slowly to a methylene chloride solution of the crude product afforded the pure dye (3.89 g, 55% yield), which was identical in all respects to material prepared as described in Example 19 above.

Example 39

Preparation of 4-[[2-amino-3-[[6-[but-2-oxy]-2-[1,1-dimethylethyl]benz[b]-4H-pyran-4-ylidene]methyl]-4-oxo-2-cyclobuten-1-ylidene]methyl]-6-[but-2-oxy]-2-[1,1-dimethylethyl]benz[b]pyrylium tetrafluoroborate This example illustrates the preparation of the dye of Formula I in which $Q^1$ is a 6-[but-2-oxy]-2-[1,1-dimethylethyl]benz[b]-4H-pyran-4-ylidene grouping, $Q^2$ is a 6-[but-2-oxy]-2-[1,1-dimethylethyl]benz[b]pyrylium grouping, and $R^1$, $R^2$, $R^3$ and $R^4$ are each a hydrogen atom.

Part A: Preparation of 2-[1,1-dimethylethyl]-6-hydroxybenz-4H-pyran-4-one

Trifluoromethanesulfonic acid (150 g) was added in a slow stream over a period of 30 minutes to a mixture of hydroquinone (30.0 g, 0.272 mol) and methyl 4,4-dimethyl-3-oxopentanoate (48.0 g, 0.304 mol) with ice/water cooling to control the mildly exothermic reaction which ensued. The reaction mixture was then warmed to 50°–55° C. and held at that temperature for 3 hours, during which time a red solution developed and, later, some solid material separated. The reaction mixture was then cooled and poured into stirred ice/water (1500 mL) containing saturated brine (100 mL), whereupon a gum separated, which solidified with scratching. This material was collected by filtration, washed with water and air-dried to give the desired compound as a pale yellow powder (46.7 g, 79% yield). The structure of this compound was confirmed by mass spectroscopy and by $^1$H and $^{13}$C NMR spectroscopy.

Part B: Preparation of 6-[but-2-oxy]-2-[1,1-dimethylethyl]benz-4H-pyran-4-one

A mixture of 2-[1,1-dimethylethyl]-6-hydroxybenz-4H-pyran-4-one (25.0 g, 0.115 mol, prepared in Part A above), 2-bromobutane (25.95 g, 0.189 mol), potassium carbonate (50.0 g, 0.36 mol) and potassium iodide (20.0 g, 0.12 mol) in MEK (250 mL) was stirred and heated at reflux under nitrogen for 8 hours. A further quantity of 2-bromobutane (8.65 g, 0.063 mol) was then added, and heating was continued for another 16 hours. The mixture was cooled and poured into stirred ice/water (1000 mL) and the mixture so formed was extracted with dichloromethane (2 400 mL aliquots). The combined organic extracts were washed with water (200 mL) and brine (200 mL), dried over magnesium sulfate and concentrated under reduced pressure to give the desired compound as a viscous, golden-brown oil (27.98 g, 89% yield). The structure of this compound was confirmed by mass spectroscopy and by $^1$H and $^{13}$C NMR spectroscopy.

Part C: Preparation of 6-[but-2-oxy]-2-[1,1-dimethylethyl]-4-methylbenzpyrylium tetrafluoroborate Methyl magnesium bromide (100 mL of a 3M solution in ether, 0.3 mol) was added over a period of 20 minutes to a solution of 6-[but-2-oxy]-2-[1,1-dimethylethyl]benz-4H-pyran-4-one (27.22 g, 0.099 mol, prepared in Part B above) in dry THF (250 mL) maintained below 10° C. with an ice/water bath; some solid material was observed to separate from the yellow-brown solution. The ice bath was removed, and the reaction mixture was stirred at room temperature for 16 hours. The mixture was then poured cautiously into a rapidly stirred solution of tetrafluoroboric acid (90 mL of a 48% aqueous solution) in ice/water (1000 mL). Vigorous effervescence was observed, and the precipitate which formed was collected by filtration, washed with water, and air-dried to yield the salt as a pale yellow powder (30.08 g, 84% yield). The structure of this compound was confirmed by mass spectroscopy and by $^1$H and $^{13}$C NMR spectroscopy.

Part D: Preparation of 4-[[2-amino-3-[[6-[but-2-oxy]-2-[1,1-dimethylethyl]benz[b]-4H-pyran-4-ylidene]methyl]-4-oxo-2-cyclobuten-1-ylidene]methyl]-6-[but-2-oxy]-2-[1,1-dimethylethyl]benz[b]pyrylium tetrafluoroborate A solution of 6-[but-2-oxy]-2-[1,1-dimethylethyl]-4-methylbenzpyrylium tetrafluoroborate (180 mg, 0.5 mmol, prepared in Part C above), 4-amino-3-butoxycyclobut-3-ene-1,2-dione (43 mg, 0.25 mmol, prepared in Example 38, Part A above), quinoline (762 mg, 6 mmol), and trimethylsilyl chloride (325 mg, 3 mmol) in dichloromethane (5 mL) was heated at reflux for 17 hours. The reaction mixture was then cooled to room temperature, and tetrafluoroboric acid (5 mL of a 48% aqueous solution) was added. Following this addition, the mixture was stirred rapidly for 30 minutes, during which time a precipitate formed. The precipitate was removed by filtration and reserved, while the filtrate was extracted with dichloromethane (2 25 mL aliquots). The combined organic layers were washed with water (25 mL) and concentrated under reduced pressure to yield a residue which was combined with the precipitate reserved earlier. Acetone (5 mL) was added to this combined crude material, and the resultant suspension was stirred for 17 hours. The solid material remaining was collected by filtration, washed with acetone, and air-dried to afford the dye (75 mg, 42% yield) as coppery crystals. The dye exhibited a near infra-red absorption in dichloromethane solution at 782 nm, $\epsilon$=319,000. The structure of this compound was further confirmed by mass spectroscopy.

EXAMPLES 40–43

Fifth Process of the Invention

The following Examples 40–43 illustrate the fifth process of the invention, that is to say reactions analogous to T→U shown in FIG. 4, together with a reaction analogous to S→T shown in FIG. 4.

Example 40

Preparation of 6-[but-2-oxy]-2-[1,1-dimethylethyl]-4-methylidenebenz[b]4H-pyran

This Example illustrates the reaction T→U shown in FIG. 4 carried out by means of a Peterson olefination.

Trimethylsilylmethylmagnesium chloride (5 mL of a 1M in ether, 5 mmol) was added to a solution of 6-[but-2-oxy]-2-[1,1-dimethylethyl]benz-4H-pyran-4-one (1.37 g, 5 mmol, prepared in Example 39, Part B above) in anhydrous THF (10 mL) under a nitrogen atmosphere, and the solution was heated to reflux for 3 hours. Thin layer chromatography of an aliquot indicated that the reaction was not complete, so an additional mount of trimethylsilylmethylmagnesium chloride (5 mL of a 1M in ether, 5 mmol) was added and the reaction solution was heated at reflux for a further 17 hours. An aqueous solution of sodium hydroxide was then added, and the mixture was heated at reflux for a further 1 hour, cooled, and filtered through a short plug of Celite (manufactured by Johns-Manville Corporation, Denver, Colo. 80217). The upper, organic layer was separated, dried over anhydrous magnesium sulfate and concentrated to afford the crude product as a light yellow oil (1.05 g, 77% yield). The structure of this compound was confirmed by mass spectroscopy and by $^1$H and $^{13}$C NMR spectroscopy.

Example 41

Preparation of 6-[but-2-oxy]-2-[1,1-dimethylethyl]-4-methylidenebenz[b]-4H-pyran This Example illustrates the same reaction as in Example 40 above, but carried out by use of a strong base on the corresponding 4-methyl salt.

Part A: Using Potassium t-butoxide

A solution of potassium t-butoxide (1 mL of a 1.0M solution in 2-methyl-2-propanol, 1 mmol) was added dropwise to a suspension of 6-[but-2-oxy]-2-[1,1-dimethylethyl]-4-methylbenzpyrylium tetrafluoroborate (0.36 g, 1 mmol, prepared in Example 39, Part C above) in heptanes (10 mL) under a nitrogen atmosphere. The green suspension was converted to a brown solution after stirring at room temperature for 30 minutes. The reaction mixture was stirred for an additional 30 minutes, then poured into ice/water. The organic layer was separated, dried over anhydrous magnesium sulfate and concentrated under reduced pressure to afford the product as a brown oil (0.27 g, 100% yield). This material was spectroscopically identical to that prepared in Example 40 above.

Part B: Using Potassium Hydride

A small amount of dry heptanes was added to a dispersion of potassium hydride in mineral oil. The resultant suspension was centrifuged and the upper layer was decanted to give a gray solid. This solid was dried in vacuo to afford 0.16 g of potassium hydride, which was then placed under a nitrogen atmosphere. Dry heptanes (10 mL) and 6-[but-2-oxy]-2-[1,1-dimethylethyl]-4-methylbenzpyrylium tetrafluoroborate (1.44 g, 4 mmol, prepared in Example 39, Part C above) were then added sequentially at room temperature. The solid suspension dissolved within one hour. After stirring at room temperature for an additional 1 hour, the solution was poured into ice/water, and the organic layer was separated, dried over anhydrous magnesium sulfate and concentrated under reduced pressure to afford the desired product as a brown oil (0.9 g, 82.5% yield). This material was spectroscopically identical to that prepared in Example 40 above.

Example 42

Preparation of 3-amino-4-[[6-[but-2-oxy]-2-[1,1-dimethylethyl]benz[b]-4H-pyran-4-ylidene]methyl]cyclobut-3-ene-1,2-dione This Example illustrates the reaction T→U shown in FIG. 4; the product is the aminosquaric acid derivative of Formula II in which $Q^1$ is a 6-[but-2-oxy]-2-[1,1-dimethylethyl] benz[b]-4H-pyran-4-ylidene grouping, and $R^1$, $R^3$ and $R^4$ are each a hydrogen atom. The reaction is promoted with a Lewis acid, namely aluminum chloride.

Aluminum chloride (0.66 g, 5 mmol) was added in one portion to a suspension of 4-amino-3-[but-1-oxy]cyclobut-3-ene-1,2-dione (0.676 g, 4 mmol, prepared in Example 38, Part A above) in THF (20 mL) under a nitrogen atmosphere. A light brown solution was obtained, together with a small amount of undissolved solid. A solution of 6-[but-2-oxy]-2-[1,1-dimethylethyl]-4-methylidenebenz[b]-4H-pyran (1.05 g, 3.86 mmol, prepared as described in Examples 40 and 41 above) in THF (10 mL) was then added slowly to the reaction mixture. A color change to green was observed immediately. An additional amount of aluminum chloride (1 g, 7.5 mmol) was then added, followed by dropwise addition of pempidine (12 drops overall). The resultant red reaction solution was stirred at room temperature for 17 hours, then quenched into ice/water. Addition of heptanes to the resultant mixture precipitated the desired product, which was collected by filtration, rinsed with heptanes and dried in vacuo to afford the aminosquaric acid derivative (130 mg, 9.2% yield). The structure of this compound was confirmed by mass spectroscopy and by $^1$H and $^{13}$C NMR spectroscopy.

Example 43

Preparation of 3-amino-4-[[2,6-bis-[1,1-dimethylethyl]seleno-4H-pyran-4-ylidene]methyl] cyclobut-3-ene-1,2-dione This Example illustrates reactions analogous to S→T→U shown in FIG. 4 but in which the starting material is the seleno analogue of the salt R shown in FIG. 2, in which $R^1$ is a hydrogen atom. Thus, the product is the same compound of Formula II prepared in Example 8 above.

A solution of potassium t-butoxide (1 mL of a 1.0M solution in 2-methyl-2-propanol, 1 mmol) was added dropwise to a suspension of 2,6-bis-[1,1-dimethylethyl]-4-methylselenopyrylium tetrafluoroborate (0.36 g, 1 mmol, prepared as described in copending application U.S. Ser. No. 07/696,222) in heptanes (10 mL) under a nitrogen atmosphere. The brown solid suspension was converted to a clear solution after stirring at room temperature for 30 minutes. The reaction mixture was stirred for an additional 30 minutes, then poured into ice/water. The organic layer was separated, dried over anhydrous magnesium sulfate and concentrated under reduced pressure to afford 0.27 g of a reddish-brown oil.

A solution of this brown oil in THF (14 mL) was added dropwise to a suspension of 4-amino-3-[but-1-oxy]cyclobut-3-ene-1,2-dione (0.114 g, 1 mmol, prepared in Example 38 above) and aluminum chloride (132 mg, 1 mmol) in THF (10 mL) under a nitrogen atmosphere. A red solution formed immediately after the addition. After stirring at room temperature for 17 hours, the reaction solution was quenched into ice/water. The organic layer was separated, dried over anhydrous magnesium sulfate, and concentrated under reduced pressure to afford an impure product. This product was purified by preparative thin-layer chromatography on silica gel with 10% methanol/dichloromethane as eluent to afford the desired product (30 mg, 9% yield). The structure of this compound was confirmed by mass spectroscopy and by $^1$H and $^{13}$C NMR spectroscopy.

EXAMPLES 44–53

Sixth Process of the Invention

Figure 5:
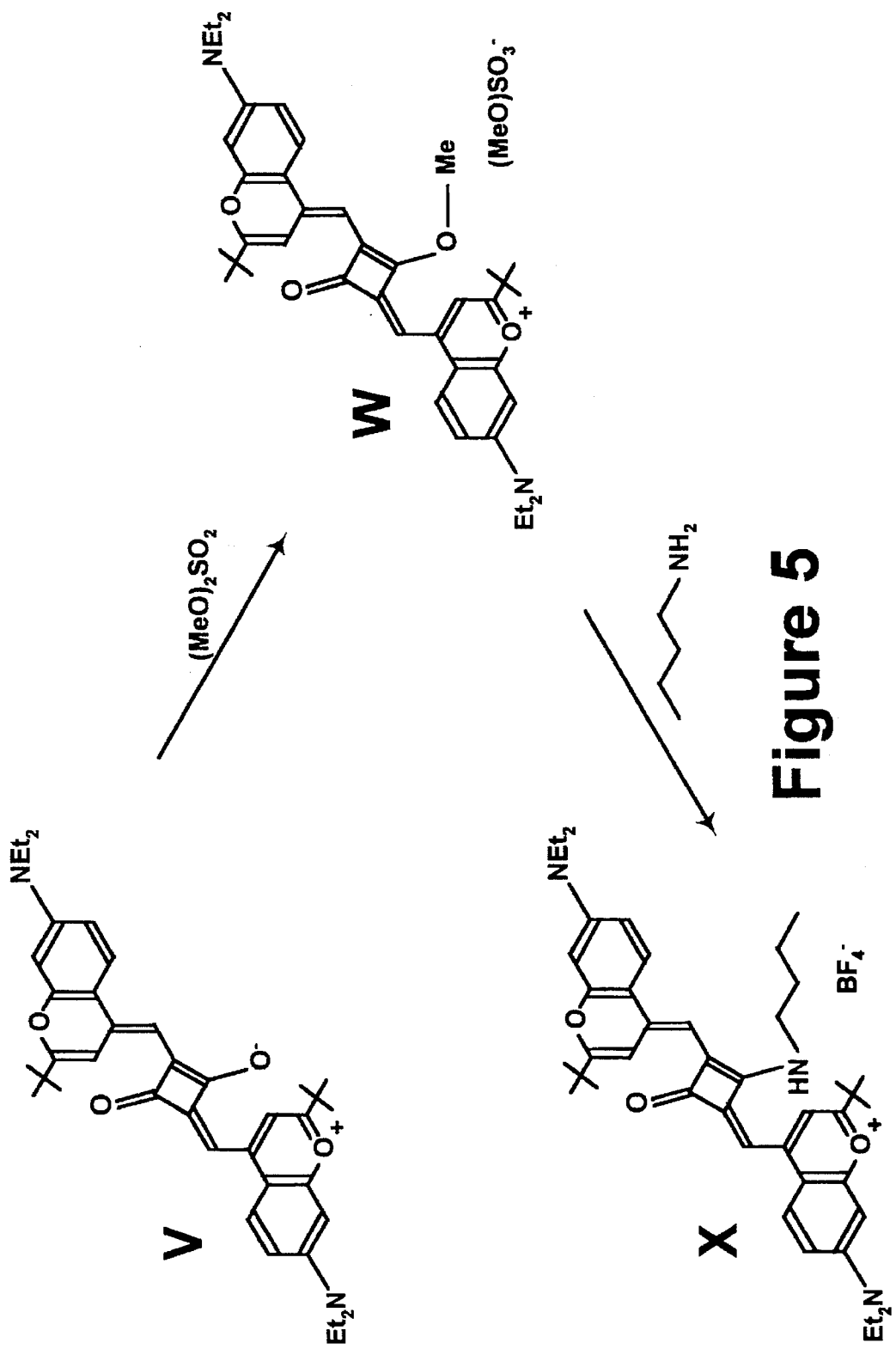
FIG. 5 shows the conversion of a 2-unsubstituted squarylium dye to a corresponding 2-aminosquarylium dye by the sixth process of the present invention.

The following Examples 44–53 illustrate the sixth process of the invention, that is to say reactions analogous to V→W and W→X shown in FIG. 5.

Example 44

Preparation of 4-[[2-butylamino-3-[[7-diethylamino-2-[1,1-dimethylethyl]benz[b]-4H-pyran-4-ylidene] methyl]-4-oxo-2-cyclobuten-1-ylidene]methyl]-7-diethylamino-2-[1,1-dimethylethyl]benz[b]pyrylium tetrafluoroborate This Example illustrates the reactions V→W and W→X shown in FIG. 5.

Part A: Preparation of 4-[[3-[[7-diethylamino-2-[1,1-dimethylethyl]benz[b]-4H-pyran-4-ylidene] methyl]-2-methoxy-4-oxo-2-cyclobuten-1-ylidene] methyl]-7-diethylamino-2-[1,1-dimethylethyl]benz [b]-pyrylium methosulfate Dimethyl sulfate (2.0 g, 15.8 mmol) was added to a solution of 4-[[3-[[7-diethylamino-2-[1,1-dimethylethyl] benz[b]-4H-pyran-4-ylidene]methyl]-2-hydroxy-4-oxo-2-cyclobuten-1-ylidene]methyl]-7-diethylamino-2-[1,1-dimethylethyl]benz[b]pyrylium hydroxide inner salt dye (1.0 g, 1.6 mmol, prepared as described in the aforementioned copending applications Ser. Nos. 07/616,639 and 07/795,038) in dichloromethane (50 mL) and the solution was stirred at reflux. Thin layer chromatography on silica gel with 10% methanol/dichloromethane as eluent indicated that trace amounts of starting material remained ($R_f$ 0.9) after 24 hours' reflux, and that a substantial quantity of the desired methylated dye had been formed ($R_f$ 0.7). The reaction mixture was accordingly worked up by washing with water (3 50 mL aliquots), and drying over anhydrous sodium sulfate, after which the solution was concentrated under reduced pressure to a volume of about 5 mL. Methyl t-butyl ether (MTBE) (15 mL) was then added to precipitate the product, which was collected by filtration, washed with MTBE and dried to afford the methylated product (1.0 g, 83% yield). This material exhibited an infra-red absorption at 786 nm in dichloromethane, $\epsilon$=426,000. The structure of this compound was confirmed by mass spectroscopy and by $^1$H NMR spectroscopy.

Part B: Preparation of 4-[[2-butylamino-3-[[7-diethylamino-2-[1,1-dimethylethyl]benz[b]-4H-pyran-4-ylidene]methyl]-4-oxo-2-cyclobuten-1-ylidene]methyl]-7-diethylamino-2-[1,1-dimethylethyl]benz[b]-pyrylium tetrafluoroborate Butylamine (42 mg, 0.575 mmol) was added to a solution of 4-[[3-[[7-diethylamino-2-[1,1-dimethylethyl]benz[b]-4H-pyran-4-ylidene]methyl]-2-methoxy-4-oxo-2-cyclobuten-1-ylidene]methyl]-7-diethylamino-2-[1,1-dimethylethyl]benz[b]pyrylium methosulfate (142 mg, 0.195 mmol, prepared in Part A above) in methylene chloride (10 mL). The resultant solution was stirred at 20° C. for 30 minutes, then washed with 10% tetrafluoroboric acid (2 4 mL aliquots), dilute aqueous sodium tetrafluoroborate, and finally dilute sodium bicarbonate (omission of the sodium bicarbonate wash results in isolation of the dye in a protonated form as indicated by a poorly resolved NMR spectrum and a bronze cast to the crystals). The organic solution was then passed through a silica gel pad followed by further elution with 10% acetone/methylene chloride (20 mL). The combined pure fractions were evaporated to a volume of 7 mL, diluted with MTBE (20 mL), stirred at 20° for 30 minutes, and filtered. The filter cake was washed with MTBE (15 mL) and dried in vacuo to yield the desired dye as a brick-red solid (88.0 mg, 60.6% yield). This dye exhibited an infra-red absorption at 810 nm in dichloromethane solution, ε=410,000. The structure of this compound was confirmed by mass spectroscopy and by $^1$H and $^{13}$C NMR spectroscopy, and was found to be identical to material prepared using a different procedure described in Example 16 above.

Examples 45–51

Preparation of Various Dyes

Example 44, Part B was repeated, except that various amino compounds were substituted for the butylamine used in Example 44, Part B, thus varying the nature of the groups $R^3$ and $R^4$ present on the 3-substituent of the squarylium ring. The amines used, the groups $R^3$ and $R^4$ present in the resultant dyes, and the wavelength of maximum near infra-red absorption ($\lambda_{max}$) of each dye are shown in Table 1 below. All the dyes were characterized by mass spectroscopy and Table 1 also shows the m/e ratio for each dye.

TABLE 1

| Ex. # | Amine | $R^3$ | $R^4$ | $\lambda_{max}$ | m/e |
|---|---|---|---|---|---|
| 45 | NH$_4$OH | H | H | 795 | 621 |
| 46 | CH$_3$NH$_2$ | CH$_3$ | H | 808 | 635 |
| 47 | n-C$_5$H$_{11}$NH$_2$ | n-C$_5$H$_{11}$ | H | 808 | 691 |
| 48 | (CH$_3$)$_2$NH | CH$_3$ | CH$_3$ | 827 | 649 |
| 49 | (C$_2$H$_5$)$_2$NH | C$_2$H$_5$ | C$_2$H$_5$ | 828 | 677 |
| 50 | (n-C$_4$H$_9$)$_2$NH | n-C$_4$H$_9$ | n-C$_4$H$_9$ | 828 | 733 |
| 51 | PhNH$_2$ (one equiv. of sodium methoxide required for reaction) | Ph | H | 801 | 696 |

Example 52

Preparation of 4-[[3-[[2,6-bis-[1,1-dimethylethyl]thio-4H-pyran-4-ylidene]methyl]-2-carboxymethylamino-4-oxo-2-cyclobuten-1-ylidene]methyl]-2,6-bis-[1,1-dimethylethyl]thiopyrylium hydroxide inner salt dye This example illustrates the preparation, by reactions analogous to V→W→X shown in FIG. 5, of the dye of Formula N (FIG. 3) in which $R^3$ is a carboxymethylamino group and $R^1$ and $R^4$ are each a hydrogen atom, this being the dye of Formula I in which $Q^1$ is a 2,6-bis-[1,1-dimethylethyl]thio-4H-pyran-4-ylidene grouping, $Q^2$ is a 2,6-bis-[1,1-dimethylethyl]thiopyrylium grouping, $R^3$ is a carboxymethyl group and $R^1$, $R^2$ and $R^4$ are each a hydrogen atom. Due to deprotonation of the carboxyl group, this dye exists as an inner salt. The amine used to form the amine group is glycine.

Part A: Preparation of 4-[[3-[[2,6-bis-[1,1-dimethylethyl]thio-4H-pyran-4-ylidene]methyl]-2-methoxy-4-oxo-2-cyclobuten-1-ylidene]methyl]-2,6-bis-[1,1-dimethylethyl]thiopyrylium tetrafluoroborate Dimethylsulfate (4.5 mL, 6.0 g, 47.6 mmol) was added to a solution of 4-[[3-[[2,6-bis-[1,1-dimethylethyl]thio-4H-pyran-4-ylidene]methyl]-2-hydroxy-4-oxo-2-cyclobuten-1-ylidene]methyl]-2,6-bis-[1,1-dimethylethyl]thiopyrylium hydroxide inner salt dye (4.50 g, 8.62 mmol, prepared as described in U.S. Pat. No. 4,508,811) in methylene chloride (75 mL). The resultant solution was stirred at reflux for 6 hours, then allowed to stand for 48 hours at 20° C., after which it was examined by thin layer chromatography to ensure complete reaction. (Silica gel plates eluted with 5% methanol in methylene chloride show the starting dye at $R_f$ 0.75 (brown fading to green) and the desired product streaking at $R_f$ 0.1–0.35. A blue impurity at $R_f$ 0.9 corresponds to an impurity in the stating material.) Sodium methoxide (7.56 g of a 25% methanolic solution, 35.0 mmol) was then added dropwise over a period of two minutes and the resulting dark brown solution was left at 20° for 3 hours (this treatment with sodium methoxide is intended to destroy residual dimethyl sulfate, a toxic methylating agent). The reaction mixture was then poured into 60 mL of ice-water containing tetrafluoroboric acid (15 mL of a 48% aqueous solution), and the organic layer was washed with dilute aqueous sodium tetrafluoroborate, stirred over solid sodium tetrafluoroborate (3.0 g) and silica gel (1.0 g) and then filtered. The filter cake was washed with methylene chloride (20 mL) and the combined filtrates were evaporated to circa 15 mL. The concentrated solution was diluted with methyl t-butyl ether (MTBE, 50 mL) and stirred at 20° for one hour, during which time a precipitate formed, which was collected by filtration. The product was washed with MTBE (20 mL) and dried in vacuo to provide the methylated dye as its tetrafluoroborate salt (4.69 g, 87.2% yield; HPLC analysis indicated a purity of 99.7% by area at 365 nm). Further dilution of the liquors with MTBE (circa 100 mL) provided an additional crop of 0.232 g (4.3%) of the methylated dye. The dye exhibited an infra-red absorption at 787 nm in dichloromethane solution, ε=330,000. The structure of this compound was confirmed by mass spectroscopy and by $^1$H and $^{13}$C NMR spectroscopy.

Alternatively, the methylated dye may be produced by using trimethyloxonium tetrafluoroborate in methylene chloride, thus providing the desired dye directly as the tetrafluoroborate salt, but the procedure gives a much less clean reaction.

Part B: Preparation of 4-[[3-[[2,6-bis-[1,1-dimethylethyl]thio-4H-pyran-4-ylidene]methyl]-2-carboxymethylamino-4-oxo-2-cyclobuten-1-ylidene]methyl]-2,6-bis-[1,1-dimethylethyl]thiopyrylium hydroxide inner salt dye Tetrabutylammonium hydroxide (1.5 mL of a 1M methanol solution, 1.50 mmol) was added to a suspension of glycine (112 mg, 1.5 mmol) in methanol (4.0 mL) and the resulting clear solution was charged at 5°–10° C. with 4-[[3-[[2,6-bis-[1,1-dimethylethyl]thio-4H-pyran-4-ylidene]methyl]-2-methoxy-4-oxo-2-cyclobuten-1ylidene]methyl]-2,6-bis-[1,1-dimethylethyl]thiopyrylium tetrafluoroborate (624 mg, 0.10 mmol, prepared in Part A above); a brown color developed. After 35 minutes the reaction mixture was quenched into 5% aqueous tetrafluoroboric acid (55 mL). The resulting black gum was washed with water (40 mL), taken up in methylene chloride (20 mL) and washed again with water, then evaporated to a red-black solid which was chromatographed on silica gel, eluting with a 15% methanol, 25% acetone, 60% dichloromethane mixture, to give 1.0 g of a brick-red partial solid, partial gum. A 300 mg portion of this gum was deprotonated by dissolution in dichloromethane, washing with dilute sodium bicarbonate, evaporation to 2.5 mL, and dilution with MTBE (12 mL). The resulting precipitate was collected by filtration and washed with MTBE (10 mL), then concentrated under reduced pressure to furnish the desired product as brick-red, fine prisms (91.2 mg, 52.4% yield). Further dilution of the mother liquors with MTBE (50 mL) provided a second crop of 53.2 mg (30.6%) of product.

The dye exhibited an infra-red absorption at 828 nm in dichloromethane solution, ε=285,000. The structure of this compound was confirmed by mass spectroscopy and by $^1$H and $^{13}$C NMR spectroscopy.

Example 53

Preparation of 4-[[3-[[2,6-bis[1,1-dimethylethyl] thio-4H-pyran-4-ylidene]methyl]-4-oxo-2-[2-phenyleth-1-ylamino]-2-cyclobuten-1-ylidene] methyl]-2,6-bis-[1,1-dimethylethyl]thiopyrylium tetrafluoroborate This Example illustrates a reaction similar to that in Example 52, Part B above, but using 2-phenylethylamine to produce a dye having a 3-[2-phenylethyl] grouping.

Addition of 2-phenyleth-1-ylamine (from the hydrochloride salt and triethylamine) to 4-[[3-[[2,6-bis-[1,1-dimethylethyl]thio-4H-pyran-4-ylidene]methyl]-2-methoxy-4-oxo-2-cyclobuten-1-ylidene]methyl]-2,6-bis[1,1-dimethylethyl]thiopyrylium tetrafluoroborate using conditions analogous to those of Example 52, Part B above provides the dye N (FIG. 3) in which $R^3$ is a 2-phenyleth-1-ylamino group and $R^1$ and $R^4$ are each a hydrogen atom, this being the dye of Formula I in which $Q^1$ is a 2,6-bis-[1,1-dimethylethyl]thio-4H-pyran-4-ylidene grouping, $Q^2$ is a 2,6-bis[1,1-dimethylethyl]thiopyrylium grouping, $R^3$ is a 2-phenyleth-1-yl group and $R^1$, $R^2$ and $R^4$ are each a hydrogen atom.

The dye exhibited an infra-red absorption at 816 nm in dichloromethane solution, ε=276,000. The structure of this compound was confirmed by mass spectroscopy and by $^1$H and $^{13}$C spectroscopy.

Example 54

Effect of Deprotonation on Position of Principal Absorptions of Cationic Amino Dyes Near infra-red absorption spectra were measured for certain cationic dyes of this invention in a neutral solvent (approximately 3 mL), and the measurements was repeated for a solution of the dye in the same solvent with the addition of a strong organic base, DBU (approximately 10 mg). The positions of the principal infra-red absorptions are indicated in Table 2 below.

TABLE 2

| Dye of Example # | Solvent | $\lambda_{max}$, neutral | $\lambda_{max}$, base |
|---|---|---|---|
| 16 | dichloromethane | 797 | 854 |
| 17 | dichloromethane | 802 | 866 |
| 18 | dimethyl sulfoxide | 829 | 897 |

From the data in Table 2, it will be seen that deprotonation of the dye, presumably from the nitrogen attached to the squarate ring, causes a shift to longer wavelength of the principal infra-red absorption by about 60 nm.

Example 55

Imaging

This Example illustrates the use of a dye of the present invention in a thermal imaging medium and process.

The thermal imaging media used in this Example was a simplified model of that described above with reference to FIG. 6. A coating fluid A was prepared by combining the infra-red dye of Formula IR4 (1.8 mg, prepared in Example 9 above) with acetone (0.73 mL), the leuco dye of Formula LD3 above (110 mg) and a polymeric binder (polyurethane Estane 5715, supplied by B. F. Goodrich, 0.73 mL of a 15% solution in acetone). Similarly, a coating fluid B was prepared by combining the infra-red dye of Formula IR6 above (1.8 mg, prepared in Example 21 above) with dichloromethane (0.18 mL), the leuco dye of Formula LD3 above (103 mg) and Estane 5715 (0.72 mL of the acetone solution). The fluids were coated onto a 4 mil (101 μm) transparent poly(ethylene terephthalate) base using a #12 coating rod. The films thus formed were laminated at 180° F. (88° C.) and 60 psi (0.4 MPa) to additional sheets of 4 mil (101 μm) poly(ethylene terephthalate) which had been coated with Joncryl 138 (supplied by S.C. Johnson & Son, Inc., Racine, Wis. 53403) to a thickness of approximately 2 μm. The resultant imaging media (hereinafter designated Media A and B respectively) exhibited peak absorptions in the near infra-red at 848 nm, absorbance 0.93 (coating A) and 805 nm, absorbance 1.51 (coating B). Storage of samples of these structures at 60° C. for 4 days resulted in losses of only 9.7% and 2.4%, respectively, of near infra-red absorptions for Media A and B.

A portion of Medium A which had not been heated was exposed to infra-red radiation from a GaAlAs semiconductor diode laser emitting at 867 nm, which delivered 62 mW to the medium. The laser output was focussed to a spot approximately 33×3 microns in size. The medium was wrapped around a drum whose axis was perpendicular to the incident laser beam. Rotation of the drum about its axis and simultaneous translation of the drum in the direction of the axis caused the laser spot to write a helical pattern on the medium. The pitch of the helix was 33 microns, chosen so that none of the medium was left unexposed between adjacent turns of the helix. In this arrangement, the exposure received by the medium was inversely proportional to the speed of rotation of the drum (here measured as a linear writing speed at the medium surface). Table 3 below shows the relationship between writing speed and red optical density (measured using an X-Rite 310 photographic densitometer, supplied by X-Rite, Inc., Grandville, Mich., with the appropriate filter) achieved. The unexposed medium had a red density of 0.07.

Similarly, a portion of Medium B which had not been heated was exposed to infra-red radiation from a GaAlAs semiconductor diode laser emitting at 792 nm, which delivered 151 mW to the medium. Table 3 shows the relationship between writing speed and red optical density achieved. The unexposed medium had a red density of 0.075.

TABLE 3

| Writing speed, m/s | Red optical density |
|---|---|
| Medium A | |
| 0.14 | 0.48 |
| 0.125 | 0.62 |
| Medium B | |
| 0.43 | 0.22 |
| 0.32 | 1.54 |
| 0.25 | 2.95 |
| 0.18 | 4.08 |

From these results, it will be seen that these thermal imaging media were capable of producing images when exposed to near infra-red radiation. Medium B produced images with optical densities as high as those needed in commercial transparencies.

We claim:

1. A process for the preparation of a 1,3-disubstituted-2-amino or substituted amino squarylium dye of the formula:

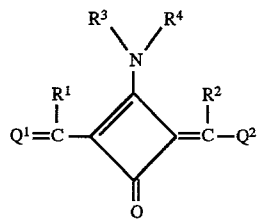

in which $Q^1$ and $Q^2$ are each a pyrylium, thiopyrylium, selenopyrylium, benzpyrylium, benzthiopyrylium or benzselenopyrylium nucleus, $R^1$ and $R^2$ are each independently a hydrogen atom or an alkyl group containing no more than about 6 carbon atoms, and $R^3$ and $R^4$ are each independently a hydrogen atom, or an alkyl or acyl group containing not more than about 6 carbon atoms, or one of $R^3$ and $R^4$ is a hydrogen atom and the other is an alkyl sulfonyl group wherein the alkyl group contains not more than about 4 carbon atoms, or a toluenesulfonyl group, or $R^3$ and $R^4$ together form a hydrocarbon group such that $R^3$ and $R^4$ together with the intervening nitrogen atom form a nitrogenous heterocyclic ring containing no hetero atoms other than said intervening nitrogen atom, which process reacting the corresponding 1,3-disubstituted-2-unsubstituted squarylium dye with an alkylating agent to produce a corresponding 1,3-disubstituted-2-alkoxy squarylium compound, and thereafter reacting the 2-alkoxy compound with ammonia or a primary or secondary amine to produce the 1,3-disubstituted-2-amino or substituted amino squarylium dye.

2. A process according to claim 1 wherein the alkylating agent used is a dialkyl sulfate.

* * * * *